US 8,858,885 B2

(12) United States Patent
Raynor et al.

(10) Patent No.: US 8,858,885 B2
(45) Date of Patent: Oct. 14, 2014

(54) PIXEL-TYPE BIOLOGICAL ANALYSIS DEVICE, BIOSENSOR, AND FABRICATION PROCESSES THEREOF

(75) Inventors: Jeffrey M. Raynor, Edinburgh (GB); Michael Maurin, Marseille (FR); Mitchell O'Neal Perley, Santa Barbara, CA (US); Pierre-Francois Lenne, Marseille (FR); Hervé Rigneault, Allauch (FR); Renaud Vincentelli, Marseille (FR)

(73) Assignees: STMicroelectronics (R&D) Limited, Buckinghamshire (GB); Universite Paul Cezanne Aix Marseille III, Aix En Provence Cedex 1 (FR)

( * ) Notice: Subject to any disclaimer, the term of this patent is extended or adjusted under 35 U.S.C. 154(b) by 860 days.

(21) Appl. No.: 12/970,615

(22) Filed: Dec. 16, 2010

(65) Prior Publication Data
US 2011/0158853 A1  Jun. 30, 2011

Related U.S. Application Data

(63) Continuation-in-part of application No. PCT/FR2009/000765, filed on Jun. 24, 2009.

(30) Foreign Application Priority Data

Jun. 27, 2008 (FR) ..................................... 08 03627
Jun. 27, 2008 (FR) ..................................... 08 03639

(51) Int. Cl.
*G01N 21/01* (2006.01)
*C40B 50/14* (2006.01)
*G01N 21/64* (2006.01)
*B01J 19/00* (2006.01)

(52) U.S. Cl.
CPC .... *G01N 21/6454* (2013.01); *B01J 2219/00596* (2013.01); *B01J 2219/00659* (2013.01); *B01J 2219/00653* (2013.01); *B01J 2219/00713* (2013.01); *B01J 2219/00725* (2013.01); *C40B 50/14* (2013.01); *B01J 2219/00585* (2013.01); *B01J 2219/00576* (2013.01); *B01J 2219/00527* (2013.01); *B01J 2219/00677* (2013.01); *B01J 2219/00497* (2013.01); *B01J 2219/00644* (2013.01); *B01J 19/0046* (2013.01)
USPC ................... 422/82.05; 422/68.1; 422/82.08; 422/82.09; 435/287.1; 435/287.2; 156/60; 156/242

(58) Field of Classification Search
USPC .......... 422/82.05, 68.1, 82.06–82.09; 156/60, 156/242, 282; 435/287.1, 287.2
See application file for complete search history.

(56) References Cited

U.S. PATENT DOCUMENTS 4,168,979 A   9/1979  Okishi et al.
5,164,319 A   11/1992 Hafeman et al.
(Continued)

FOREIGN PATENT DOCUMENTS

WO   98/01221 A1   1/1998
WO   2004/050243 A1  6/2004

OTHER PUBLICATIONS

Libera et al. (MRS Proceedings vol. 954 Jan. 2007.*

*Primary Examiner* — Jan Ludlow
(74) *Attorney, Agent, or Firm* — Seed IP Law Group PLLC

(57) ABSTRACT

The disclosure relates to a pixel-type biological analysis device comprising a photosensitive layer, a capture mixture for the capture of targeted proteins, the capture mixture being placed on an external surface of the photosensitive layer and comprising a protein probe grafted to a hydrogel, collection means for collecting photoelectrons in the photosensitive layer, and reading and treatment means of an electrical quantity supplied by the collection means, for the supply of a characteristic value of a luminous intensity detected by the photosensitive layer.

18 Claims, 11 Drawing Sheets

(56) References Cited

U.S. PATENT DOCUMENTS

| | | |
|---|---|---|
| 5,234,566 A | 8/1993 | Osman et al. |
| 5,837,454 A | 11/1998 | Cozzette et al. |
| 5,846,708 A | 12/1998 | Hollis et al. |
| 6,325,977 B1 * | 12/2001 | Theil ............ 422/82.05 |
| 6,710,370 B2 | 3/2004 | Street et al. |
| 6,953,925 B2 | 10/2005 | Fang et al. |
| 6,998,659 B2 | 2/2006 | Raynor |
| 7,384,797 B1 | 6/2008 | Blair |
| 7,579,077 B2 | 8/2009 | Dubrow et al. |
| 7,585,664 B2 * | 9/2009 | Chan et al. ............ 435/287.2 |
| 7,601,557 B2 | 10/2009 | Baek |
| 7,919,828 B2 | 4/2011 | Rhodes et al. |
| 8,044,586 B2 | 10/2011 | Wang et al. |
| 8,264,014 B2 | 9/2012 | Rothberg et al. |
| 8,274,040 B2 | 9/2012 | Zhong et al. |
| 2002/0031813 A1 | 3/2002 | Ozkan et al. |
| 2003/0146100 A1 | 8/2003 | Huang et al. |
| 2009/0013768 A1 | 1/2009 | Pouteau et al. |
| 2009/0066345 A1 | 3/2009 | Klauk et al. |
| 2009/0267167 A1 | 10/2009 | Pouteau et al. |
| 2009/0298704 A1 | 12/2009 | Anwar et al. |
| 2010/0298895 A1 | 11/2010 | Ghaffari et al. |

* cited by examiner

PIXEL-TYPE BIOLOGICAL ANALYSIS DEVICE, BIOSENSOR, AND FABRICATION PROCESSES THEREOF

BACKGROUND

1. Technical Field

The present disclosure relates to a pixel-type biological analysis device.

The present disclosure equally relates to a complementary metal oxide semiconductor (CMOS) biosensor comprising a plurality of pixel-type biological analysis devices arranged in a matrix of pixels. The present disclosure equally relates to a fabrication process of a pixel-type biological analysis device and a fabrication process of a CMOS biosensor comprising a plurality of biological analysis devices with pixels arranged in a matrix of pixels.

2. Description of the Related Art

The present disclosure relates, in a general manner, to improvements of biological analysis techniques such as described in U.S. Pat. No. 6,325,977 or in international application WO 2006/082336.

These techniques use pixel-type biological analysis devices comprising:

a photosensitive layer and collection means for collecting photoelectrons in the photosensitive layer, and means for reading and treating an electrical quantity supplied by the collection means for the provision of a characteristic value of a luminous intensity detected by the photosensitive layer.

In these prior art references, conventional and commercial charge-coupled device (CCD) or CMOS imagers are utilized for studying solid molecular organic structures, that is to say structurally stable and resistant to even extreme experimental conditions, such as for example oligonucleotides (RNA, DNA, etc.). In these applications, the oligonucleotides can be directly grafted onto an external surface of the biosensors. However, the biosensors realized with such imagers are much less adapted to more fragile structures such as proteins that easily loose their functionalities, either by modification of their three-dimensional structure or by denaturation, under the effect of temperature or of dehydration. The intrinsic properties of biomolecules of this family are such that their study in a standardized, multiplexed and miniaturized way (in the format of a biosensor) is at this time still delicate. However, these intrinsic properties may allow applications to be provided in the domains of infectious disease diagnostic testing, allergies, pollutants, drug detection, defense, etc.

Thus, it may be desired to have a biological analysis device suitable for use for structures more fragile than those of oligonucleotides contemplated in the state of the art.

BRIEF SUMMARY

An embodiment of the disclosure relates to a pixel-type biological analysis device comprising: a photosensitive layer; a capture mixture for the capture of targeted proteins, the capture mixture being placed on an external surface of the photosensitive layer and comprising a protein probe grafted to a hydrogel; collection means for collecting photoelectrons in the photosensitive layer; and means for reading and treatment of an electrical quantity supplied by the collection means, for the supply of a characteristic value of a luminous intensity detected by the photosensitive layer.

According to one embodiment, the external surface of the photosensitive layer is of a sufficient size to receive the totality of a pre-determined dose of protein probe in the form of a drop.

According to one embodiment, the external surface of the photosensitive layer has a surface of at least $25500 \times 10^{-12}$ m$^2$.

According to one embodiment, the photoelectron collection means comprise several island-shaped collection zones and spaced one from the other in the photosensitive layer.

According to one embodiment, the collection zones are spaced one from the other in the photosensitive layer at a distance less than a maximum pre-determined distance set as a function of a recombination distance of photoelectrons emitted in the photosensitive layer.

According to one embodiment, the photosensitive layer comprises: a first portion, fitted with a first area of the collection means, able to detect an incident luminous intensity coming from a capture mixture and supplying a first electrical quantity; a second portion, fitted with a second area of the collection means, protected against the incident luminous intensity coming from the capture mixture and supplying a second electrical quantity; and in which the reading and treatment means comprise treatment means combined with the first and second electrical quantities for the supply of a characteristic value of a luminous intensity detected by the first portion of the photosensitive layer.

An embodiment of the disclosure relates to a fabrication process of a biological analysis device such as described above, characterized in that it comprises the steps of: preparing the external surface of the photosensitive layer intended to receive the capture mixture, comprising a step of silanization of the external surface; oxidation of the hydrogel and grafting of the oxidized hydrogel on the silanized external surface; carboxylation and activation of the grafted hydrogel; and grafting of the protein probe in the activated hydrogel.

According to one embodiment, the step of preparation of the external surface by silanization comprises the steps of: cleaning the external surface by successive rinsings with demineralized water, acetone and pure ethanol in an ultrasonic bath; alkaline oxidation of the external surface by oxidation under an ozone plasma, then treatment by a solution of potassium hydroxide during several hours at an ambient temperature; successive submersions in demineralized water then in pure ethanol under ultrasound and drying under an Argon flow; silanization of the external surface via a solution of 3-aminopropyltriethoxysilane in ethanol during several hours; successive submersions in demineralized water then in pure ethanol under ultrasound and drying under an Argon flow; and heating of the device during several hours then maintaining under an inert atmosphere.

According to one embodiment, the step of oxidation and of grafting of the hydrogel comprises the steps of: dissolution of the hydrogel in demineralized water, then treatment by a solution of sodium periodate of which the volume is adjusted in order to obtain a mixture of which the molar ratio between the sodium periodate and a pre-determined repetitive monomer pattern of the hydrogel is on the order of 50%; protection of the obtained reaction mixture against light and agitating during several hours at ambient temperature, to obtain an oxidized hydrogel; grafting of the oxidized hydrogel on the silanized external surface and agitating at ambient temperature and protected from light during several hours; treatment of the obtained ensemble by an aqueous solution of sodium cyanoborohydride during several hours in order to reduce formed Schiff bases, then rinsing in demineralised water, ethanol and drying under Argon flow.

According to one embodiment, the step of carboxylation and of activation of the grafted hydrogel comprises the steps of: treatment of the grafted hydrogel by a solution of bromoacidic acid in sodium periodate during several hours at ambient temperature and under Argon; draining of the obtained reaction mixture then rinsing in demineralized water, ethanol and drying under Argon flow; activation under the form of esters of formed carboxylate residue, then rinsing with water.

According to one embodiment, the process comprises a preliminary step of treatment of the external surface of the photosensitive layer intended to receive the capture mixture with the aid of a hydrophobic coating of which the roughness is chosen such that at least one solution deposited on the photosensitive layer during the preparation of the capture mixture does not spread out beyond the photosensitive layer.

According to one embodiment, the process comprises a step consisting of sizing the external surface of the photosensitive layer intended to receive the capture mixture such that it corresponds to the size of a pre-determined dose of the capture mixture likely to be placed on the external surface in the form of a drop.

An embodiment of the disclosure relates to a biosensor comprising a plurality of pixel-type biological analysis devices such as described above arranged in a matrix of pixels and a treatment circuit of signals supplied as outputs of the matrix of pixels.

According to one embodiment, each pixel of the matrix of pixels comprises an analogue to digital signal converter for the digital conversion of the characteristic value of a luminous intensity detected by the photosensitive layer of this pixel, and the treatment circuit of signals supplied on output of the matrix of pixels comprises a digital data transmission bus connected to converters of pixels of the matrix.

According to one embodiment, each pixel is separated from an adjacent pixel by an insulation joint shaped to electrically insulate the photosensitive layer of the pixel from the photosensitive layer of the adjacent pixel.

According to one embodiment, the biosensor presents a contact surface with a fluid to analyze, this surface comprising: a first central zone in which a matrix of pixels is arranged, covered by a hydrophobic coating; a first peripheral zone surrounding the central zone, comprising electronic circuits and covered by a hydrophilic coating; a second peripheral zone surrounding the first peripheral zone, comprising electric contact pads and covered by a hydrophobic coating; and a bio-compatible resin barrier covering the second peripheral zone, fixed on the hydrophilic coating.

According to one embodiment, the hydrophilic coating is silicon oxide.

According to one embodiment, the hydrophobic coating is silicon nitride.

BRIEF DESCRIPTION OF THE SEVERAL VIEWS OF THE DRAWINGS

Examples of implementation of the disclosure will be described in greater detail in the following description, in relation with but not limited to the following figures, in which:

FIGS. 9a, 9b, 9c, 9d show in further detail various embodiments of the differential pixel structure.

DETAILED DESCRIPTION

In the description that follows, various specific details are given for a better understanding of embodiments of the disclosure. The embodiments described may be implemented without one or several of these details, or by using other methods, equipment, materials, etc. In certain cases, materials or operations that are in and of themselves well known are not described in detail in order to not obfuscate certain aspects of the described embodiments. The reference to an "embodiment" in the descriptions signifies that a characteristic or a particular structure described in relation with this embodiment is included in this embodiment. Thus, the utilization of expressions "in one embodiment" or "according to one embodiment" in various parts of the description are not necessarily referring to the same embodiment. Moreover, the particular characteristics relative to each embodiment may be combined in an appropriate manner to form one or more other embodiments. Lastly, the analysis, commentary, deductions and conclusions stated in the following in relation with the prior art are considered to be an integral part of the present disclosure.

Figure 1:
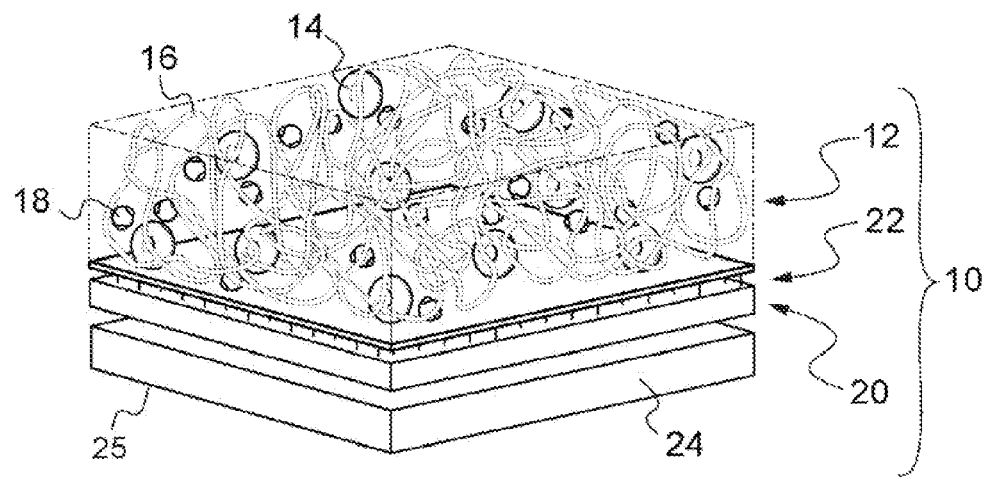
FIG. 1 shows schematically the structure of one embodiment of a biological analysis device according to the disclosure.

FIG. 1 shows the general structure of a biological analysis device 10 and of a biosensor according to one embodiment of the disclosure. The biological analysis device 10 is made on a semiconductor substrate 25. It comprises a layer of a capture mixture 12 comprising a certain quantity of a protein probe 14 grafted to a hydrogel 16, 18 and intended to capture a certain type of target protein. The hydrogel comprises a hydrophilic medium 16 incorporating water molecules 18, such as for example Dextran (registered trademark), nitrocellulose, hyaluronic acid or else a derivative of these saccharine polymers or polyamide. More generally, this hydrogel is a natural or synthetic polymer capable, according to its formulation, of retaining up to 99% water.

Each molecule of the protein probe 14 is adapted to couple with a corresponding molecule of the target protein likely to be found in a substance to be analyzed. In the case of coupling of the two molecules, when a third marked molecule is added and associated with the targeted molecule, for example a secondary antibody, a quantity of light can be emitted, for example by chemiluminescence or by fluorescence.

The biological analysis device 10 also comprises a photosensitive layer 20. This photosensitive layer comprises an external surface 22 onto which a capture mixture layer 12 is deposited. This photosensitive layer 20 is adapted to absorb photons emitted by chemiluminescence or by fluorescence from the capture mixture 12 and to collect photoelectrons with the aide of at least one collection zone not shown in FIG. 1. This is done by a photodiode for example. More precisely, the external surface 22 is treated, for example by silanization, to allow the deposition of the capture mixture 12 and notably the hydrogel 16, 18 on the photosensitive layer 20.

Finally, the biological analysis device 10 comprises electrical read circuitry 24 for the reading and the processing of an electrical quantity supplied by the collection means of the photosensitive layer 20, and for supplying a signal characteristic of a luminous intensity detected by the photosensitive layer. This electronic circuitry, shown schematically here, is embedded in the semiconductor substrate 25 and is configured to realize a transfer of charges generated in the photosensitive layer 20.

The biological analysis device 10 permits an analysis of a biological substance susceptible of including a certain quantity of the target protein corresponding to the grafted protein probe 14, with the aide, for example, of a chemiluminescence detection protocol.

This chemiluminescence detection protocol comprises the following steps:
  the biological substance may be treated or not by an analysis agent in order to chemically break down certain of its components: this step renders certain molecules of the biological substance accessible to molecules of the protein probe 14 and therefore capable of being analyzed; the obtained mixture is then deposited on the capture mixture layer 12 of the biological analysis device 10 comprising the protein probe 14, then incubated for a variable duration depending upon the treated species,
  a solution of "secondary" antibodies coupled to a chemiluminescence marker, for example the HorseRadish Peroxidase (HRP) enzyme, is added and the ensemble is incubated for several minutes: this antibody couples in a specific manner and with a strong affinity for couples formed by molecules of the protein probe and the target protein; the concentrations and the duration of incubation can vary and are optimized according to the targeted application in a known manner,
  several cleanings are then performed in order to eliminate all traces of the secondary antibody adsorbed in a non-specific manner at the surface of the biological analysis device 10 and which may cause a false detection; the types of cleaning (time, composition, concentration, number) are variable and may be adapted in a known manner according to the proteins used during the detection protocol,
  an activation of a chemiluminescence signal and a corresponding detection by the biological analysis device 10 is realized by the addition of a developer solution of the specific substrate of the HRP enzyme in optimal concentration conditions and of a pH for a chemiluminescence signal: this developer solution may be commercially obtained or prepared, for example in the form of luminol; it is added over the entire surface of the biological analysis device 10 and the signal is immediately collected by the photosensitive layer 20,
  a post-processing computation may be used in order to amplify the obtained signal,
  finally, the comparison of the luminous intensity value obtained by the biological analysis device 10 with a pre-determined calibration curve, or determined at the same time as that of the biological measurement, allows for the estimation of the quantity of the target protein present in the biological substance sample.

The biological analysis device 10 may also be used to proceed with the analysis of a biological substance with the aide of a fluorescence detection protocol. Such a fluorescence detection protocol comprises the same steps as that of the chemiluminescence detection protocol except that the secondary antibody is coupled to a fluorophore instead of to a chemiluminescence marker and that an excited light is brought about instead of a developer solution for the activation of a fluorescence signal.

Figure 2:
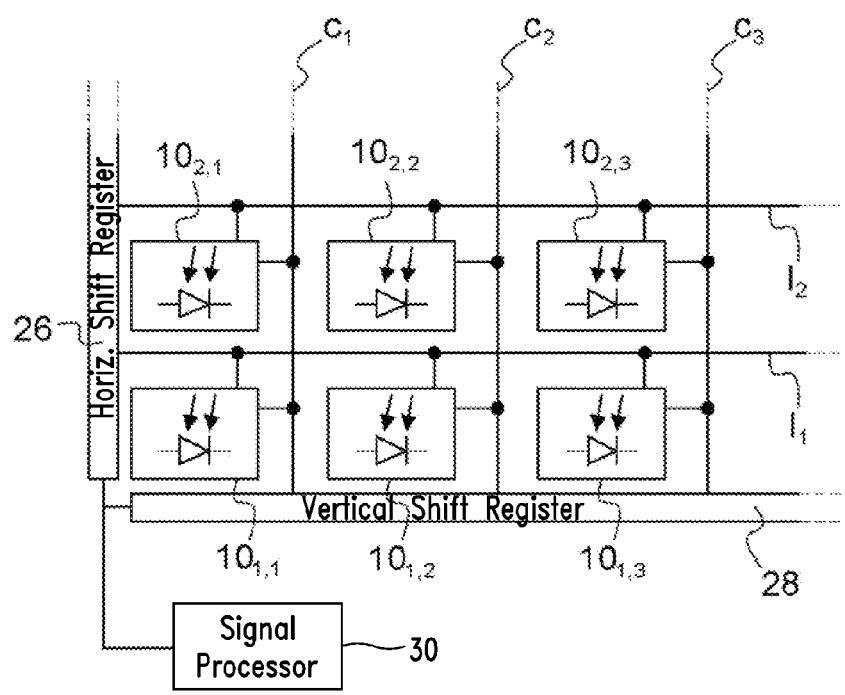
FIG. 2 is the electric diagram of a biosensor comprising a plurality of devices such as that shown in FIG. 1, FIGS. 3a, 3b, 3c are flow charts showing successive steps of a fabrication process of the device of FIG. 1.

As shown in FIG. 2, several devices $10_{i,j}$, such as device 10 of FIG. 1, may be arranged in a pixel matrix of a biosensor. Each device $10_{i,j}$ forms a pixel of line i and of column j of the matrix. In FIG. 2, only the first two lines and first three columns of a pixel matrix are shown, but it is easy to generalize this representation to m lines and n columns in order to form a complete biosensor.

The pixels $10_{1,1}$, $10_{1,2}$ and $10_{1,3}$ are linked to a bus of the first line $I_1$ and the pixels $10_{2,1}$, $10_{2,2}$ and $10_{2,3}$ to a bus of the second line $I_2$ for the transmission of luminous intensity values. The buses of lines $I_1$ and $I_2$ are linked to a horizontal shift register 26. Pixels $10_{1,1}$ and $10_{2,1}$ are linked to a bus of the first column $c_1$, the pixels $10_{1,2}$ and $10_{2,2}$ to a bus of the second column $c_2$ and the pixels $10_{1,3}$ and $10_{2,3}$ to a bus of the third column $c_3$ for the transmission of luminous intensity values. The buses of columns $c_1$, $c_2$ and $c_3$ are linked to a vertical shift register 28. The shift registers 26 and 28 are linked to a signal processing circuit 30 which may notably comprise a digital signal circuit.

To make a biosensor with a pixel matrix, structures other than that which has just been described in reference to FIG. 2 may be envisaged. Notably, each pixel may be fitted with its own analog to digital converter. Examples of such structures will be described later with reference to FIGS. 6a, 6b and 6c.

The capture mixture 12 is made in two steps on the biosensor, in a conventional manner. In a first step, the hydrogel 16 is deposited over the entire surface of the biosensor. In a second step, a specific solution of protein probes 14 is deposited locally in the form of a drop. Several different protein probes can thus be deposited on the same hydrogel substrate, drop by drop, each drop comprising a specific protein probe. An experiment has shown that a drop of several nanoliters of a protein probe can be sufficient to allow for the photodetection by chemiluminescence or by fluorescence of a target protein, which corresponds to a drop of approximately 150 μm (micrometers) in diameter. Below this size, either the evaporation at the time of the deposition of the protein probe solution becomes too large and does not allow the protein probes to be maintained, or else the quantity of the protein probe is insufficient to allow for a photodetection by chemiluminescence (or by fluorescence).

In the prior art, taking into account the size of the pixels of a conventional biosensor, largely less than 150 μm, a drop of a specific protein probe covers a plurality of pixels of a biosensor due to the fact that their small size, in general around ten pixels, and the electric signals obtained by the plurality of pixels of the biosensor must be combined by a posteriori processing in order to obtain an indication value of the quantity of the target protein in the biological samples. This a posteriori processing is complex and may be filled with errors. In addition, in order to avoid that the luminous intensity sources by chemiluminescence or by fluorescence interfere between two drops of neighboring specific protein probes, the drops of the protein probe must be spaced at a sufficient distance. In general, this distance can be up to three times the size of a drop of the protein probe, approximately 450 μm. A non-negligible photosensitive surface area in the biosensor is lost in this manner.

According to a preferred embodiment of the disclosure, each pixel is advantageously dedicated to the detection of a particular target protein and presents a photosensitive surface area that has dimensions greater than those of a conventional imager, adapted to the size of such a drop. Each pixel presents for example a length of 150 μm or more (for a pixel with a square shape) corresponding to a surface on the order of 25500 μm$^2$ or more (i.e., 25500.10$^{-12}$ m$^2$ or more). As previously indicated, this surface corresponds to the size of a drop of the protein probe below which the evaporation during the deposition becomes too great and does not allow the protein probes to be maintained, or the quantity of the protein probe is insufficient to allow photodetection by chemiluminescence or by fluorescence. Without these constraints, a pixel could reach much smaller sizes, such as 20 μm×20 μm for example.

Thus, a drop of specific protein probe 14 is placed on the hydrogel substrate 16 above each biological analysis device, that is to say above each pixel $10_{i,j}$ of the biosensor matrix in a manner so as to avoid any a posteriori processing as previously described.

The detection protocol by chemiluminescence or by fluorescence may easily be adapted to the biosensor shown in FIG. 2, by considering each pixel of this biosensor as a biological analysis device such as the analysis device 10 previously described. In this case, each pixel comprises its own type of protein probe and the biological substance eventually chemically decomposed is deposited over the entire external photosensitive surface of the biosensor. At the end of the protocol, the comparison of values of luminous intensity obtained for each pixel (therefore for each type of protein probe of each pixel) with a pre-determined calibration curve, or determined at the same time as the biological measurement, allows a large quantity of distinct proteins to be quantified from the biological substance sample.

More precisely, for the calibration of the proteins to be quantified, a range of protein solutions with known increasing concentrations is systematically analyzed by the biosensor in the same conditions as those of a real biological test. The pixel value for each of the analyzed concentrations is then placed on a graph as a function of the protein concentration, or stored in a memory on the biosensor. During the real biological test, it suffices to compare the obtained pixel value with the graph previously traced, or with the value previously stored, to obtain an estimation of the concentration of the target protein in the tested biological sample.

Deposition of the Capture Mixture

An embodiment of certain steps of a fabrication process of a biological analysis device according to the disclosure will now be described with reference to FIGS. 3a, 3b and 3c. These steps aim to deposit a capture mixture layer 12 on the external surface 22 of the photosensitive layer 20.

Figure 3A:
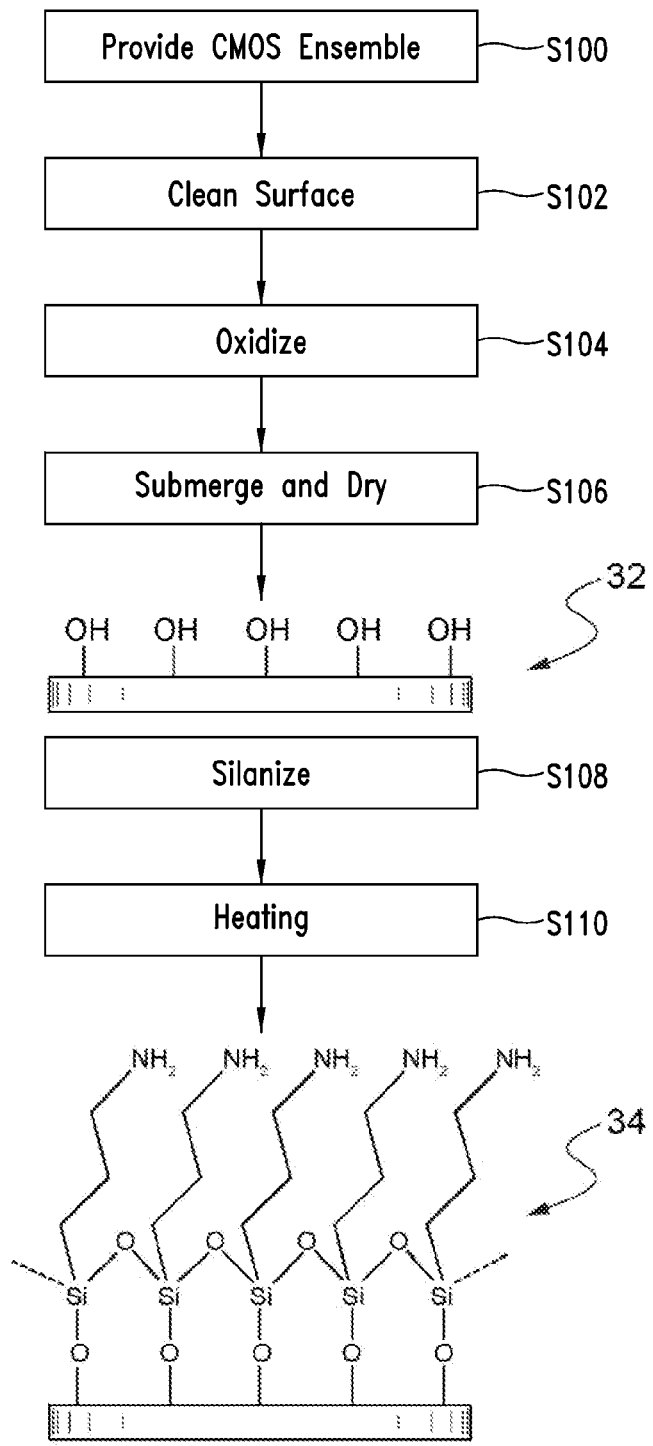
Figure 3B:
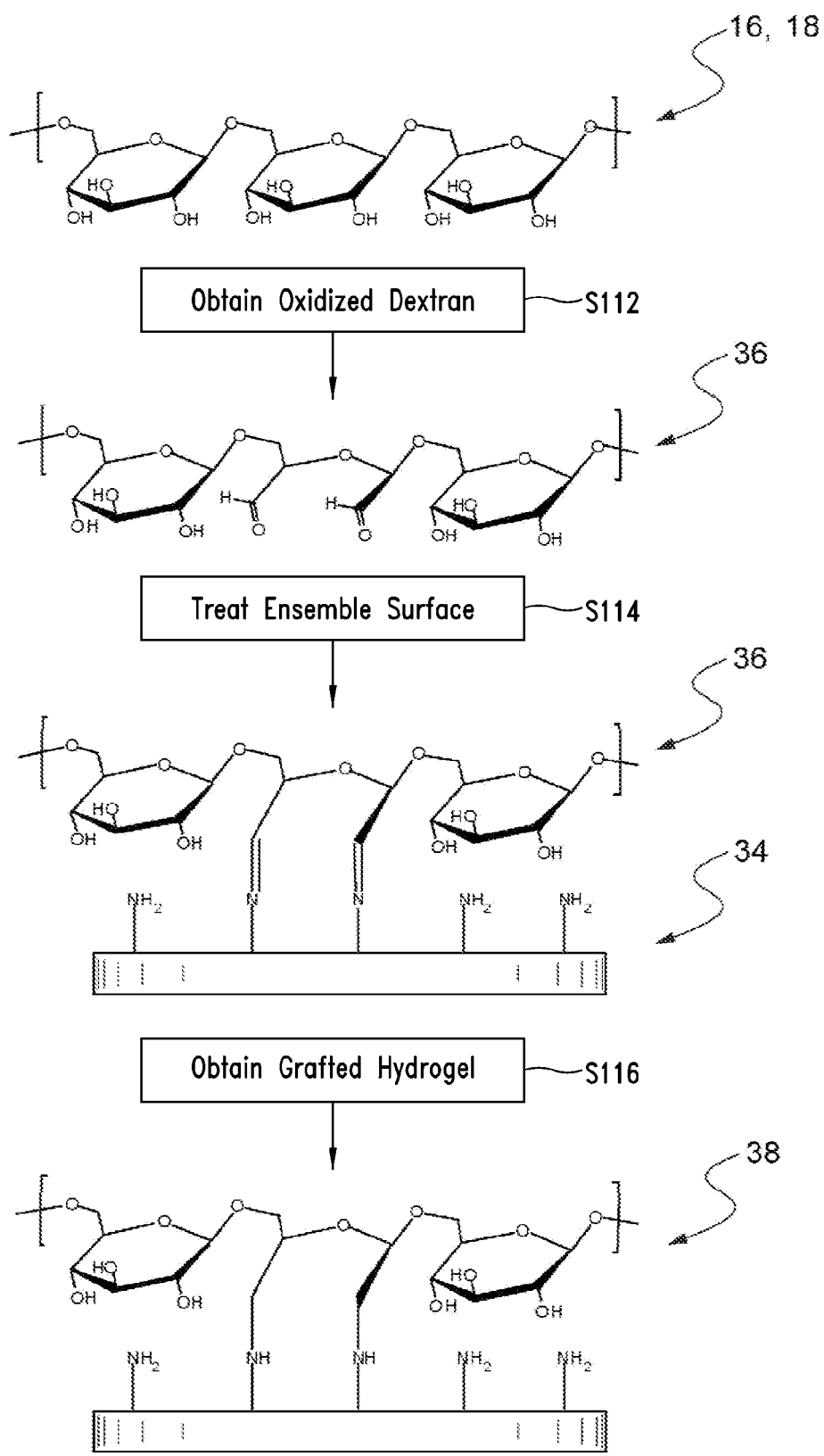

As shown in FIG. 3a, during a first step S100, an electronic CMOS ensemble is supplied comprising a photosensitive layer 20 and electronic read circuitry 24 for the reading and the processing of an electrical quantity supplied by the photosensitive layer 20 (FIG. 1). The external surface 22 of the photosensitive layer eventually comprises a hydrophobic coating, for example of the type $Si_3N_4$ that will be described later.

Next, during a step S102, the external surface 22 of the photosensitive layer 20 of the CMOS electronic ensemble is cleaned by successive rinsings in demineralized water, in pure acetone and ethanol in an ultrasonic bath.

During a step S104, the external surface 22 is oxidized by means of an ozone plasma, for example during 15 minutes, then treated by a solution of KOH 2.2M in an aqueous mixture, for example a mixture $H_2O/EtOH$ (2:3), for example during 3 hours at an ambient temperature.

During a step S106, the CMOS electronic ensemble is then submerged successively in demineralized water then in pure ethanol under ultrasound before being dried in an Argon flow.

During a step S108, silanol residue 32 formed on the external surface 22 are silanized by an APTES solution in ethanol 0.4M, for example during 12 to 20 hours, at an ambient temperature and an inert atmosphere (Argon).

Then the CMOS electronic ensemble is again cleaned several times with demineralized water in an ultrasonic bath, rinsed with pure ethanol and dried under an Argon flow.

It is then heated, for example at 85° C., during several hours, for example 5 hours, then maintained in an inert atmosphere during a step S110, to finally obtain a silanized external surface 34. As shown in FIG. 3b, a hydrogel 16, 18, for example Dextran (0.5 g, molecular weight of approximately 100 kiloDalton), is dissolved in 50 ml of demineralized water, then treated by a solution of $NaIO_4$ 0.1M of which the volume is adjusted in order to obtain a mixture of a mole ratio between the moles of $NaIO_4$ and the moles of Dextran glucose monomers of the order of 50%, during a step S112. It can indeed be observed in FIG. 3b that Dextran is a polymer of which the base pattern is a glucose derivative. Thus, it is a matter of adjusting the volume of the $NaIO_4$ 0.1M solution so that it has two times as many molecules of the base pattern of Dextran than of $NaIO_4$ molecules. The opening of every other base pattern in the Dextran is thus obtained, as illustrated when leaving step S112 in FIG. 3b.

The reaction mixture is protected from the light and vigorously agitated during several hours at an ambient temperature, for example 20 hours, so as to obtain oxidized Dextran 36.

Next, during a step S114, the silanized external surface 34 is treated by the recently prepared oxidized Dextran solution 36. The reaction is agitated at an ambient temperature and protected from light during 48 hours for example.

The reaction mixture is then drained during a step S116 and the CMOS electronic ensemble is treated by an aqueous solution of $NaBH_3CN$ 0.1M during for example 3 hours in order to reduce the formed Schiff bases. After aspiration of the suspension, the CMOS electronic ensemble is intensively rinsed in demineralized water then in ethanol and dried under an Argon flow, in order to obtain a grafted hydrogel 38.

Figure 3C:
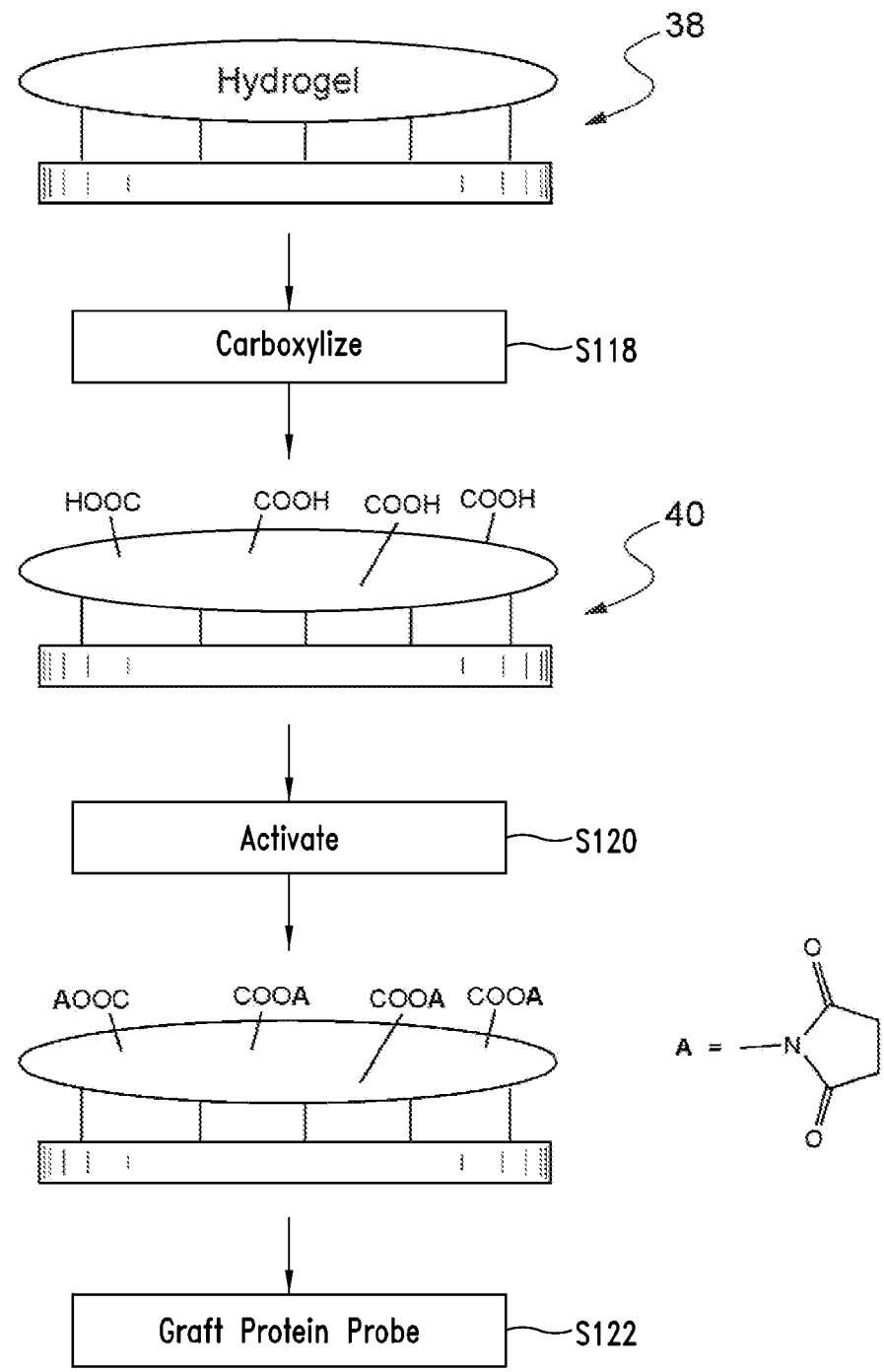

As shown in FIG. 3c, the grafted hydrogel 38 is then carboxylized and activated. In order to do this, during a step S118, it is treated with a solution of $BrCH_2COOH$ 0.1M in NaOH 2M during for example 16 hours at an ambient temperature and under Argon. Once this oxidation is finished, the reaction mixture is drained and the sensor is rinsed in demineralized water and ethanol, then dried under an Argon flow.

The formed carboxylate residues 40 are then activated in esters during a step S120, for example by means of an aqueous solution of EDC(0.2 M)/NHS (50 mM), and for example during 15 minutes at an ambient temperature. The CMOS electronic ensemble is then abundantly rinsed in water.

Finally, during a last step S122, an appropriate solution of the desired protein (protein probe) is grafted in the activated hydrogel.

In order to realize the fabrication of a complete biosensor such as that shown in FIG. 2, it is suitable to perform steps S100 to S120 on the group of pixels of the biosensor. At the end, the final step S122 is applied differently to each pixel for the grafting of a drop of a specific protein probe on the activated hydrogel substrate above the pixel.

It can be noted that the usual abbreviations utilized above:
(CH3)2O: Acetone
C2H5OH or EtOH: Ethanol
O3: Ozone
KOH: Potassium Hydroxide
NaOH: Sodium Hydroxide
H2O: Water
Ar: Argon
"APTES": 3-Aminopropyltriethoxysilane or (H2N(CH2)3Si (OEt)3)
NaIO4: Sodium Periodate
NaBH3CN: Sodium Cyanoborohydride
BrCH2COOH: Bromoacetic acid
EDC: 1-ethyl-3-(3-dimethylaminopropyl) carbodiimide hydrochloride
NHS: N-Hydroxysuccinimide.

Improvements of a biological analysis device and of a biosensor according to the disclosure or a fabrication process of such a biosensor will now be described. These improvements may be implemented separately or in combination, at the choice of the skilled person, and as a function of the desired result and technical or economic constraints that will eventually be taken into account for the realization of biosensors according to the disclosure.

Provision of a Differential Pixel Structure

In the biological analysis device 10 previously described, the photosensitive layer 20 comprised for example a doped region within the semiconductor substrate 25 (FIG. 1). The energy of an incident photon extracted from the electrons of atoms situated in the photosensitive layer 20 generates a charge and thus a current. The photosensitive layer 20 of the biological analysis device 10 uses an electric field in a P-N junction to cause the separation of an ion and a photoelectron and to prevent a recombination and loss of signal. However, these P-N junctions present a small current loss that the photosensitive layer 20 cannot distinguish from a current that is generated by an incident luminous intensity, in this case by chemiluminescence or by fluorescence. This loss current is equally present in the absence of light and as such is commonly called "dark current". The use of the term dark is understood as being a condition in which an incident luminous intensity is either absent or does not cause the photogeneration of charges in the photosensitive layer 20 of the biological analysis device 10. This may be due to a protection of the photosensitive layer preventing the passage of incident light, or due to the maintenance of the photosensitive layer 20 at a certain potential, for example an initialization potential, which prevents the accumulation of charges.

This dark current is a limiting factor upon the performance of the biological analysis device 10 or more generally of the CMOS-type biosensor. The dark current depends strongly upon the temperature and is therefore difficult to offset. It varies considerably with the absence of uniformity in the doping gradients. Improvements aiming to suppress this dark current are particularly advantageous for the biological analysis device or for the aforementioned biosensor, given that the luminous intensity emitted by chemiluminescence or by fluorescence is generally very weak. In this type of application, it is important that the biological analysis device or that the biosensor is very sensitive.

Figure 4A:
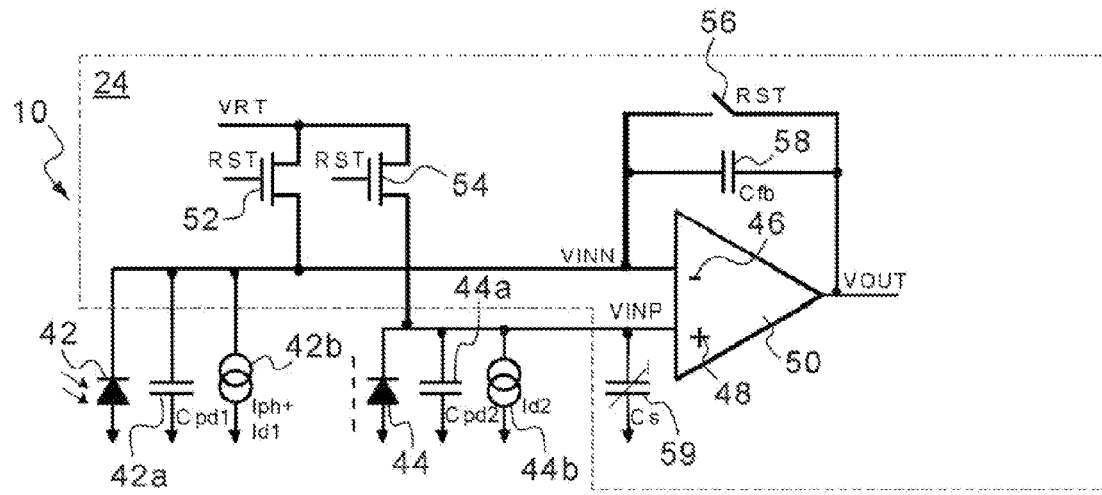
FIG. 4a shows an embodiment of electronic means for a biological analysis device according to the disclosure.

FIG. 4a is an electric diagram of an embodiment of the biological analysis device 10 having an improved sensitivity.

The biological analysis device 10 includes a photosensitive layer 20 comprising a first photosensitive portion 42 and a second photosensitive portion 44. The photosensitive portions 42, 44 emit signals applied to the electronic read circuitry 24. In this example embodiment, the signal supplied by the photosensitive portion 42 is applied to an inverting input 46 of an operational amplifier 50 and the signal supplied by the photosensitive portion 44 is applied to a non-inverting input 48 of the amplifier 50. The photosensitive portions are represented by photodiodes, but any other type of photosensitive sensor may be used.

The first photosensitive portion 42 is suitable for detecting an incident luminous intensity coming from the capture mixture 12 (FIG. 1) by the chemiluminescence or fluorescence effect, while the second photosensitive portion 44 is protected from the incident luminous intensity coming from the capture mixture 12 or from all other sources of luminous intensity. Even though the second photosensitive portion 44 is protected against all sources of luminous intensity, it is still considered to be "photosensitive" in that it is made the same material and displays the same electrical characteristics as the first photosensitive portion 42. Thus, if it were not protected against light, it would generate, as the first photosensitive portion 42, a charge in response to all incident light. For example, each of the first and second photosensitive portions may comprise photodiodes that, in an embodiment of the disclosure, may have identical forms. An independent opaque protection is therefore formed above the second photosensitive portion 44. For the sake of clarity in the remaining description, the first photosensitive portion 42 will be known as the lighted photosensitive portion, while the second photosensitive portion 44 will be known as the darkened photosensitive portion.

The biological analysis device 10 realized in this manner can therefore be described as a "differential pixel" in contrast with a pixel which does not have these two photosensitive portions of which one is protected from incident light.

The protection applied to the darkened photosensitive portion 44 is obtained thanks to mechanical means, for example by the deposition of a metal or of another opaque substance above this photosensitive portion 44, either directly on the external surface, or as a layer separated from the photosensitive portion 44 thanks to an appropriate passivation layer. A metallic layer or other layer, separated from the external surface by a passivation layer, is advantageous to reduce the coupling capacitance between the metallic protection and the photodiode of the darkened photosensitive portion 44. On the other hand, this type of protection does not prevent the passage of a luminous intensity arriving on the sides.

Alternatively, the opaque layer may be removed and replaced with a mechanical barrier erected between the lighted photosensitive portion 42 and the darkened photosensitive portion 44, in such a way that the capture mixture 12 is constrained to rest above the lighted photosensitive portion 42 without going over onto the darkened photosensitive portion 44. Consequently, the output of the darkened photosensitive portion 44 only represents a dark current in the sense that no reaction of chemiluminescence or of fluorescence taking place in the capture mixture 12 generates a luminous intensity susceptible of being captured by the darkened photosensitive portion 44.

Yet alternatively, the mechanical protection may take the form of an opaque box of the biological analysis device 10 that may comprise several portions arranged in such a manner so as to cover a surface appropriate to define the darkened photosensitive portion 44.

Each photosensitive portion 42, 44 of the photosensitive layer 20 is connected to an initialization voltage VRT by intermediary MOS switches 52 and 54 respectively. These switches 52 and 54 are shown in FIG. 4 as NMOS transistors but can be implemented as PMOS transistors or any other type of appropriate switch. An initialization switch 56 is also supplied in parallel with a feedback capacitor 58 having a capacitance Cfb, which is also placed in parallel between the output and the inverting input 46 of the operational amplifier 50. The initialization switch 56 can be selectively controlled in order to discharge the operational amplifier 50.

Preferably, the lighted photosensitive portion 42 and the darkened photosensitive portion 44 are as similar as possible in order to generate dark currents as similar as possible. The constraints imposing this, as well as the different possibilities for their arrangement, will be detailed below.

For this, an adjustable capacitor 59 having a capacitance Cs is added between the ground and the non-inverting input 48 of the operational amplifier 50.

In FIG. 4a, the photosensitive portion 42 is modeled as a capacitor 42a having a capacitance Cpd1 representing the intrinsic capacitance of photosensitive portion 42, in parallel with a current source 42b. Likewise, the photosensitive portion 44 is modeled as a capacitor 44a having a capacitance Cpd2 representing the respective intrinsic capacitance of the photosensitive portion 44, in parallel with a current source 44b. For the lighted photosensitive portion 42, the current source 42b supplies a current Iph+Id1, Iph being the current generated by the chemiluminescence or by the fluorescence effect and Id1 being the dark current generated by the photodiode. For the darkened photosensitive portion 44, the current source 44b only supplies a current Id2, that is to say the dark current which traverses it.

At the non-inverting input 48 of the operational amplifier 50, the current and voltage values conform to the following equation:

$(Cpd2+Cs)(\delta VINP/\delta t)+Id2=0$ (equation 1)

At the inverting input 46 of the operational amplifier 50, the current and voltage values conform to the following equation:

$-Cpd1\ \delta VINN/\delta t + Cfb(\delta VOUT/\delta t - \delta VINN/\delta t) - (Iph+Id1)=0$ (equation 2)

By rearranging the previous equation, the following equation is obtained:

$(Iph+Id1)+(Cpd1+Cfb)\delta VINN/\delta t - Cfb\ \delta VOUT/\delta t = 0$ (equation 3)

At the output of the operational amplifier 50, there is, in a general case, the following relationship:

$\delta VOUT/\delta t = (IPH(Cs+Cpd2)+Id1(Cs+Cpd2)-Id2(Cpd1+Cfb))/(Cfb(Cs+Cpd2))$ (equation 4)

From equation 4, it can be deducted that in the general case, the effect of the dark current on the output voltage can be removed if the following equation is verified:

$Id1(Cs+Cpd2)=Id2(Cpd1+Cfb)$ (equation 5)

In particular, equation 5 can be satisfied and the dark current effect canceled if:

$Id1=Id2$, and $(Cs+Cpd2)=(Cpd1+Cfb)$ (equation 6)

In other words, it can be deduced from equations 5 and 6 that the dark current effect is canceled when the product between the dark current in the lighted photosensitive portion 42 and the sum of the capacitance Cs of the adjustable capacitor 59 and of the intrinsic capacitance Cpd2 of the darkened photosensitive portion 44 is equal to the product of the dark current in the darkened photosensitive portion 44 and the sum of the capacitance Cfb of the feedback capacitor 58 of the operational amplifier 50 and of the intrinsic capacitance Cpd1 of the lighted photosensitive portion 42. In particular, the dark current effect is canceled in the output voltage if the dark current is the same in the two photosensitive portions 42 and 44 and if the sum of the adjustable capacitance Cs and of the intrinsic capacitance Cpd2 of the darkened photosensitive portion 44 is equal to the sum of the capacitance Cfb of the feedback capacitor 58 of the operational amplifier 50 and of the intrinsic capacitance Cpd1 of the lighted photosensitive portion 42.

Additionally, the operational amplifier 50 can be conceived so as to present a high common mode rejection ratio so that the signals that appear on both inputs are ignored. This signifies that any noise on the ground is ignored and does not appear at the output.

Figure 4B:
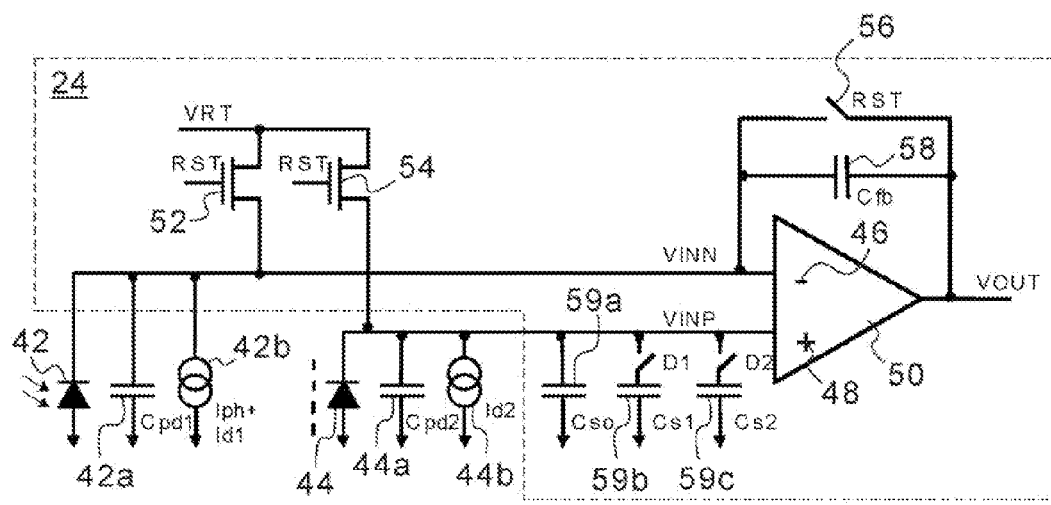
FIG. 4b shows another embodiment of electronic means for a biological analysis device according to the disclosure.

On this basis, there are several options in order to conceive a biological analysis device 10 corresponding to that of FIGS. 4A, 4B. The first is to make the photosensitive portions 42 and 44 identical and to regulate the adjustable capacitor 59 in order to obtain the equality (Cs+Cpd2) =(Cpd1+Cfb). Assuming that Cpd1=Cpd2, this amounts to setting the adjustable capacitance Cs to the same value as that of the capacitance Cfb of the feedback capacitor 58. Several techniques assuring the correspondence of the photosensitive portions will be discussed below.

It can be noted that the dark current is very sensitive to the profile and to precise amounts of doping of the substrate in which it circulates, although in fact a difference exists between these parameters between neighboring pixels or even between two photosensitive portions of a same pixel.

Another complication comes from the structural differences between the adjustable capacitance Cs, on one hand, and the feedback capacitance Cfb, on the other hand. In particular the adjustable capacitor 59 has a terminal connected to the ground while the operational amplifier 50 requires that the two terminals of the capacitor 58 are floating. Because these structures are different, it is difficult to make them correspond.

Equation 5 shows that even if these currants Id1 and Id2 do not correspond, the dark current effect can always be canceled as long as the products Id1 (Cs+Cpd2) and Id2 (Cpd1+Cfb) are equal.

FIG. 4b shows an embodiment of a biological analysis device 10 that comprises means for obtaining the adjustable capacitance Cs and canceling the dark current effect even if the currents Id1 and Id2 are not equal.

In this figure, the elements that are identical to those shown in FIG. 4a are designated by the same references.

The difference between these two figures resides in the configuration of the adjustable feedback capacitance Cs, which is not shown here as a single capacitor 59 but as a plurality of capacitors 59a, 59b, 59c connected in parallel between the ground and the non-inverting input 48 of the operational amplifier 50. Capacitor 59a has a capacitance Cs0 and is permanently connected between the ground and the non-inverting input 48 of the operational amplifier 50. Capacitor 59b has a capacitance Cs1 and capacitor 59c has a capacitance Cs2. These capacitors are selectively connected between the ground and the non-inverting input 48 of the operational amplifier 50, by means of switches D1 and D2. Capacitance Cs0 presents a value inferior to that of Cfb. Even though only three feedback capacitors are shown in FIG. 4b in a purely illustrative and non-limiting manner, a larger number may be used.

Thus, in one embodiment, the values of Cs0, Cs1 and Cs2 are chosen so that Cs1=Cs2 and Cs0+Cs1=Cfb. Consequently, if the dark current Id1 is slightly greater than the dark current Id2, then, in order to maintain the equality anticipated by equation 5, Cs should be less than Cfb. This is obtained by leaving the switches D1 and D2 open so that Cs=Cs0 and is less than Cfb. If the two dark currents Id1 and Id2 are identical, switch D1 is opened and switch D2 is closed. Therefore, it results that Cs=Cs0+Cs1=Cfb. If the dark current Id1 is slightly less than the dark current Id2, in order to maintain the equality of equation 5, Cs should be greater than Cfb. This is obtained by closing the switches D1 and D2 so that the adjustable capacitance Cs is equal to Cs0+Cs1+Cs2.

This method can also be applied in the case where, even though the dark currents of the two photosensitive portions 42 and 44 are identical, a slight difference between the values of Cfb and Cs0 is tolerated.

In one embodiment, the capacitors of the plurality of capacitors in parallel have the same value, so that the adjustable capacitance Cs can be incremented by a constant value. The number of capacitors in the plurality of capacitors can be increased in order to increase the resolution or the amplitude of variations that can be expected.

In an alternative manner, the capacitors of the plurality of capacitors in parallel can have different values in order to increase the flexibility of the ensemble. For example, in an embodiment, a factor two is introduced between each successive capacitance of the parallel arrangement, which allows the number of switches to be limited. By thus supplying a non-inverting input capacitance of base value Cs0 and capacitances equal to 1, 2, 4, 8 and 16 times an increment Cs1, a capacitance Cs which can be adjusted between Cs0 and Cs0+ 31 Cs1 with an increment equal to Cs1 is obtained.

In a more general way, using N optional switches in parallel to allow the electronic means 24 to adapt to fabrication variations that are in general of the order of +/−25%, the capacitance Cs0 is chosen to correspond with 75% Cfb and the sum Cs1+ . . . +CsN is chosen to correspond with 50% Cfb, so that the adjustable capacitance Cs can be adjusted between 75% Cfb and 125% Cfb. The inequality of the dark currents Id1 and Id2 is not often known in advance and a calibration phase may be used in order to determine it. This calibration can be performed as part of a post-fabrication test applied to the biological analysis device 10 and the configuration of the switches can be saved in memory. On the contrary, the calibration can also be done <<on the fly>> just before the device is put into service.

The output voltage VOUT can be measured by any appropriate technique, for example with the use of an analog to digital converter or by using device 10 in a light/frequency operating mode, in which the output voltage VOUT is compared to a reference signal causing a re-initialization of device 10 when it is reached. The output voltage is thus given by the frequency of initial pulses.

As was previously seen, it is preferable for the suppression of the dark current effect that the first and second photosensitive portions 42 and 44 correspond as closely as possible. However, in practice, even if identical photosensitive portions are fabricated, the dark current can differ slightly from one to the other due to factors intervening during their fabrication or functioning. In practice, the respective dark currents of the two photosensitive portions are often different and it is difficult to attain an exact equality. A realistic objective is thus to try to minimize this difference.

The minimization of this difference can be obtained by the device shown in FIG. 4b. However, the resolution of this system is limited by the number and value of the capacitors provided in the capacitive ensemble arranged in parallel at the non-inverting input of the operational amplifier 50.

Figure 5:
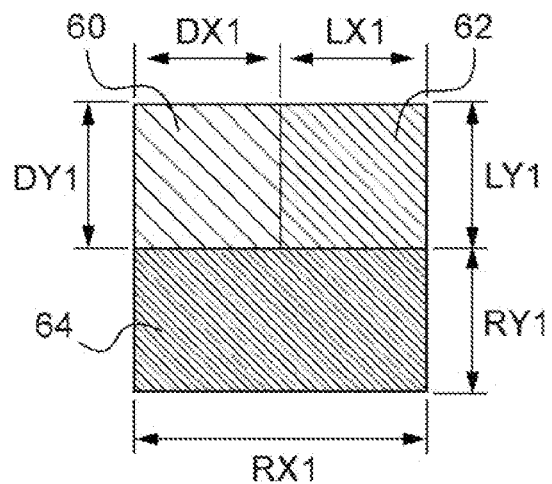
FIG. 5 shows schematically a differential pixel structure usable in a biological analysis device according to the disclosure.

Another factor that can be factored in is the geometry of the biological analysis device 10 and the geometry of the ensemble of biological analysis devices as pixels in a biosensor. An example pixel geometry is shown in FIG. 5 in a view from below.

In this figure, a darkened photosensitive portion 60 is situated in an upper left area of the pixel. It is adjacent to a lighted photosensitive portion 62 situated in an upper right area of the pixel. The electronic read circuitry 64 of this pixel is situated in a lower area of the pixel underneath the photosensitive portions 60 and 62.

For a good correspondence between the photodiodes, the dimensions of the photosensitive portions 60 and 62 can be equal (DX1=LX1 and DY1=LY1) in which case RX1=DX1+ LX1. Additionally, the photosensitive portions can have square shapes (DX1=DY1). The size of RY1 depends upon the precise composition of the electronic means 64, but it is preferable that it is equal to the dimensions DY1 and LY1, so that the pixel is globally of a square shape.

On the basis of this pixel configuration, several pixels can then be situated in different manners in lines or columns to form a complete biosensor.

They can be arranged in line and in column, for example, by a simple vertical or horizontal translation of the pixel shown in FIG. 6.

Alternatively, they can also be arranged so that two successive lines of pixels are inverted vertically one in comparison with the other and thus having their respective electronic means 64 or their respective photosensitive portions 60, 62 corresponding.

Yet alternatively, instead of being square shaped, the pixels can also be rectangular, the electronic means 64 being situated below the darkened photosensitive portion 60, which is itself situated below the lighted photosensitive portion 62.

Furthermore, the photosensitive portions can be triangular to form a photosensitive layer 20 of a general square form, or of more complex forms all while having equal surfaces.

Thus, several variants can be provided by the skilled person, and will not be further detailed.

In order to realize a biosensor arranged in a differential pixel matrix, the structure described with reference to FIG. 2 can be considered, but others are also possible. Notably, each differential pixel can be fitted with its own analog to digital signal converter. It is equally possible for the non-differential pixels.

Figure 6A:
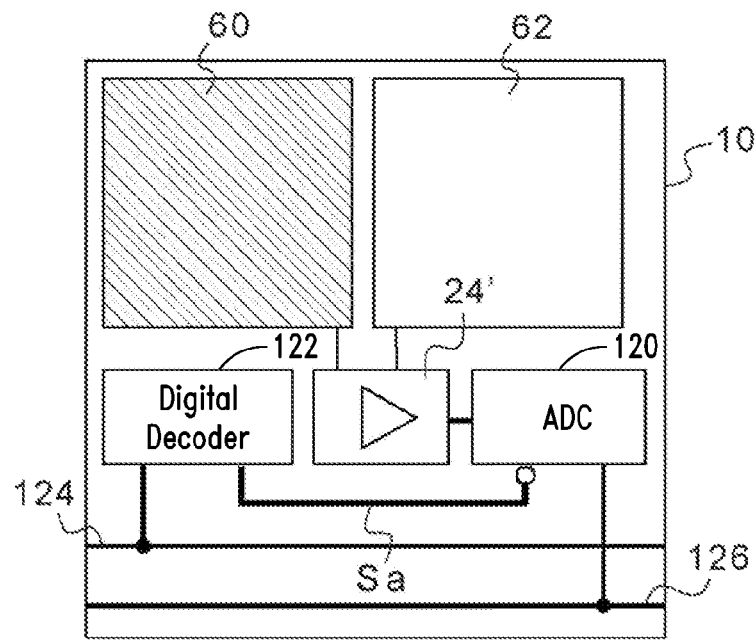
FIGS. 6a and 6b show adaptations of a differential pixel structure including an analogue/digital converter.

A first example is shown in FIG. 6a. In this figure, the differential pixel 10 comprises, on the upper side, a darkened photosensitive portion 60 and a lighted photosensitive portion 62. These two photosensitive portions are connected to an amplifier circuit 24', for example such as the electronic means 24 detailed in FIG. 4a or 4b. This amplifier circuit supplies an analog output voltage that is transmitted to the input of an analog-to-digital converter 120.

The differential pixel 10 also comprises a digital decoding block 122 the characteristics of which depend upon the coordinates of the differential pixel 10 in the pixel matrix of the biosensor. This digital decoding block 122 monitors the state of an address bus 124 such that, when a signal passing on this address bus 124 corresponds to a pre-determined value stored in the digital decoding block 122 and specific to the differential pixel 10, the block 122 transmits an activation signal Sa to the converter 120 which supplies to a data transmission bus 126, in response, a digital value of the analog output voltage of the amplifier circuit.

Figure 6B:
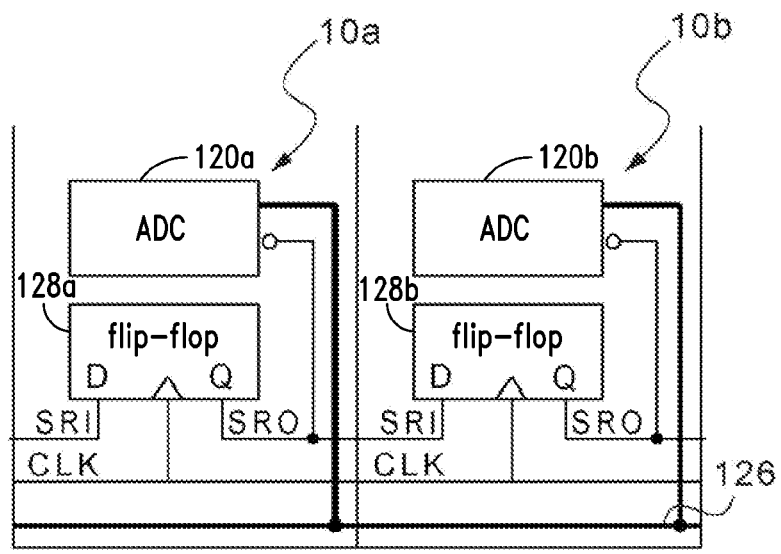

A second example, shown in FIG. 6b and showing two adjacent pixels, is a variant of the example of FIG. 6a. In order to simplify the illustration, the photosensitive portions 60 and 62 and the amplifier circuit 24' of each differential pixel are not shown even though they are present.

In this variant, the digital decoding blocks 122 are replaced by a shift register formed that includes a flip-flop in each pixel, that is to say a flip-flop 128a in pixel 10a and a flip-flop

128b in pixel 10b that are cascaded together. Only two flip-flops 128a, 128b of the shift register are shown in FIG. 6b, but it will be understood that the shift register could include any number of flip-flops, such as flip-flops of an entire row of pixels or an entire column of pixels. Each flip-flop 128a, 128b receives an input signal SRI (Shift Register Input) and supplies an output signal SRO (Shift Register Output). The output signal SRO of the flip-flop 128a forms the input signal SRI of the flip-flop 128b. Similarly, the output signal SRO of the flip-flop 128b forms the input signal of a flip-flop of the following pixel while the input signal SRI of flip-flop 128a is formed by an output signal of a flip-flop of a preceding pixel. The output signal of each flip-flop 128a, 128b is also supplied to the converter 120a, 120b corresponding to pixel 10a, 10b in a manner so as to activate this converter so that it transmits its digital value to the data transmission bus 126 at the desired time. Additionally, a clock signal CLK is supplied to the flip-flops 128a, 128b to cadence the transmissions of digital values of pixels to the data transmission bus 126.

The use of this variant comprises the following steps:
first, each pixel of the matrix of pixels is set into a logic state 0 (inactive) to block the outputs of converters 120a, 120b,
a logic state is set to 1 (active) at the input of a first pixel 10a in order to activate the clock signal for this pixel and in this way set the signal SRO of this pixel to 1, so that the converter 120a transmits its digital value output to the data transmission bus 126,
the logic state of the first pixel 10a is then set to 0 (inactive) and the clock signal is again active to activate 10b and to deactivate pixel 10a,
in the rest of the reading process of the digital values of the converters of the pixel matrix, the output signal SRO of pixel 10a remains in the "0" state and the active state of the signal SRO propagates through the matrix with each pulse of the clock.

The variant of FIG. 6b has the advantage of presenting electronic circuits that are identical for all of the pixels of the biosensor, with fewer interconnections than in FIG. 6a, so that fewer connection contacts are used to link the biosensor to an external controller. On the other hand, the reading of these digital values of the converters is less flexible because it is pre-determined by the wiring of the biosensor that cannot, by definition, be modified during the functioning. The random access made possible by the example embodiment of FIG. 6a is therefore advantageous in respects to that of the variant of FIG. 6b.

Figure 6C:
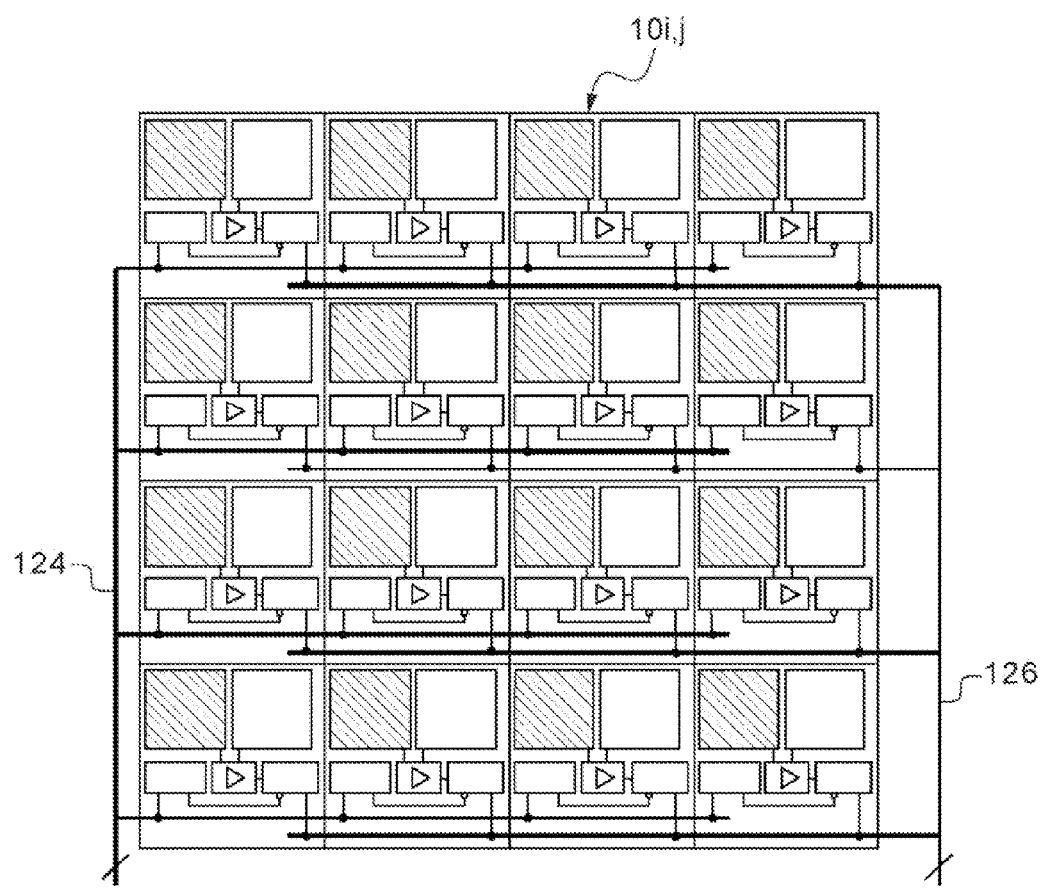
FIG. 6c is the electric diagram of a biosensor comprising a plurality of differential pixels such as those shown in FIG. 6a, FIGS. 7 and 8 show by cross-sectional views embodiments of a photosensitive layer usable in a biological analysis device according to the disclosure.

As shown in FIG. 6c, several devices 10$_{i,j}$ such as the device 10 of FIG. 6a can be arranged in a pixel matrix of a biosensor. Each device 10$_{i,j}$ forms a pixel of line i and of column j in the matrix. In FIG. 6c, only four lines and four columns of a pixel matrix are shown, but this representation can be generalized to m lines and n columns in order to form a complete biosensor.

All the pixels are connected to the same address bus 124 that determines the sequence in which the pixels of the biosensor can supply their digital output values. Similarly, all the pixels are connected to the same data transmission bus 126 that gathers the digital output values.

Prevision of a Plurality of Photoelectron Collection Zones

The differential pixel structure described with reference to FIGS. 4 to 6 is based upon the hypothesis that the photosensitive portions are defined strictly by their borders, that is to say that their external dimensions define the photoelectron collection zone. In this case, the desire for correspondence between the first and second photosensitive portions signifies that the surfaces of these two photosensitive portions should be more or less equal.

However, a possible improvement in the structure of the photosensitive layer 20 of the biological analysis device 10, and notably in the structure of the photoelectron collection means, allows for the conception of photosensitive portions of different surfaces all while assuring the correspondence of the generated dark currents.

The principle allowing the illustration of this structural improvement is described in U.S. Pat. No. 6,998,659.

Figure 7:
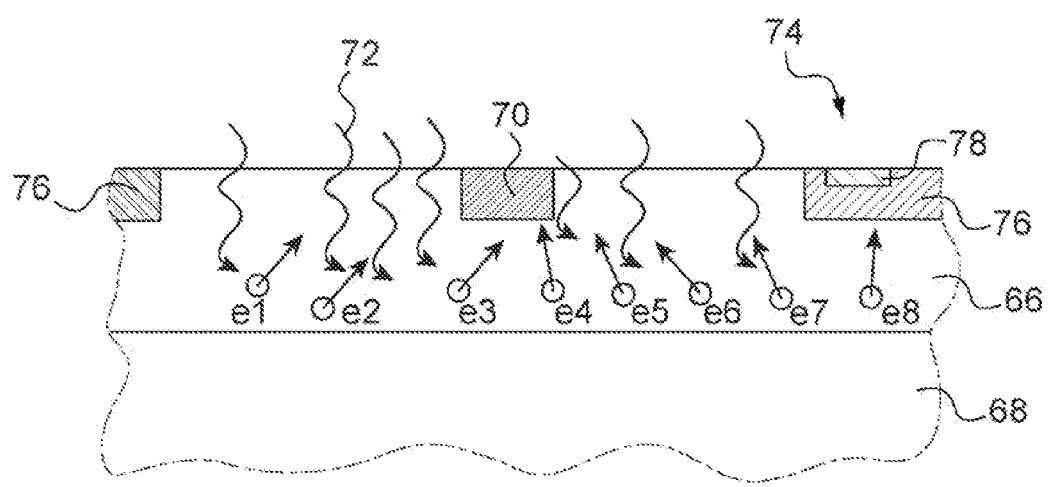

A first embodiment of a biological analysis device in accordance with the principle presented in this US patent is shown in FIG. 7. A P-epitaxial layer 66 is formed on the p substrate 68. This substrate 68 is the semiconductor substrate 25 described above or a doped region of this semiconductor substrate. A photoelectron collection zone 70 is provided, in the form of an island-shaped N-well implanted in the P-epitaxial layer 66. The collection zone 70 collects the photoelectrons e1, . . . e8 generated by an incident radiation 72, in particular a chemiluminescence or a fluorescence radiation. Electronic read circuitry 74 comprises a p-well 76 in which an NMOS transistor 78 is located.

In a conventional pixel-type biological analysis device, the n-well 70 would extend over the entire available area between the electronic means 74 of successive pixels. In the device of FIG. 7, the n-well 70 is island-shaped and is surrounded by P-epitaxial material that is not connected to ground and has a very low dopage in comparison with the p-well 76.

The small size of the n-well 70 signifies that the capacitance of the photosensitive portion is relatively low, but the efficiency is not compromised. In fact, the large majority of photoelectrons, such as the photoelectrons e1, . . . , e6 shown in FIG. 7, diffuse in the P-epitaxial layer 66 and are finally collected by the n-well 70. Electron e7 statistically can orient itself indifferently either towards the n-well 70 or else towards the p-well 76, whereas electron e8 will certainly orient itself towards the p-well 76 and be lost.

Figure 8:
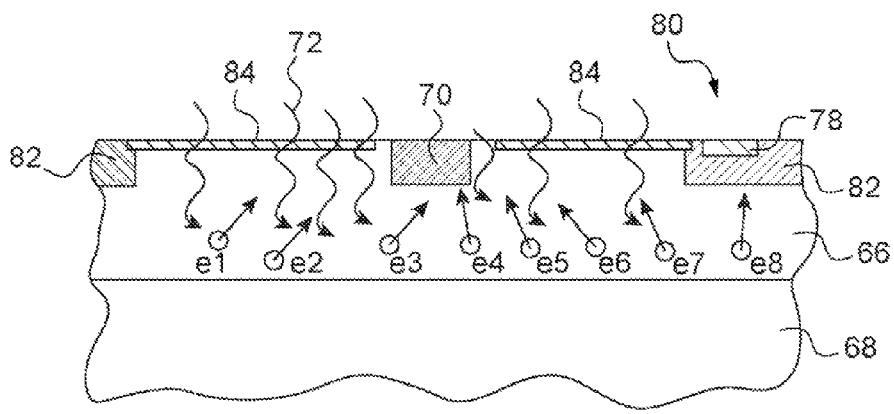

A second embodiment of the biological analysis device in accordance with the principle presented in U.S. Pat. No. 6,998,659 is shown in FIG. 8. In this embodiment, the electronic read circuitry 80 comprises a thin layer 84 of P+ material spreading out over a large area of the device, such that the surface of the P-epitaxial layer 66 around the n-well 70 is covered by this thin layer, with the exception of a narrow zone immediately around the n-well 70. The thin layer 84 spreads from a p-well 82 of the electronic means 80 and is thus connected to the p-well. The p-well 82 is in general connected to ground and the thin layer 84 as well. The thin layer 84 is also less deep and, being situated at a lower potential that that of the n-well 70, the photoelectrons have a higher chance of going towards the n-well 70 and being collected by it than by the thin layer 84 or by the p-well 82. For example, electron e7 in FIG. 8 has a higher chance of going towards the n-well 70, while in FIG. 7 it has the same chance of going towards the n-well 70 as towards the p-well P 76.

The size of a collection zone such as the n-well 70 depends upon the fabrication technology utilized, but can in general be as small as 1 μm×1 μm. However, this minimum size is not recommended because with these dimensions, fabrication hazards can cause large size differences between the collection zones which can cause larger differences in their characteristics. Since, in a differential pixel, the darkened photosensitive portion must precisely correspond to the lighted photosensitive portion, collection zones of too small sizes are not desired. On another hand, an increase of the n-well size increases the surface and its perimeter, leading to an increase of the dark current and of the associated noise. Currently, a good compromise for a collection zone such as the n-wells, taking into account the previously-mentioned constraints, is a size between 5 μm and 15 μm.

Figure 9A:
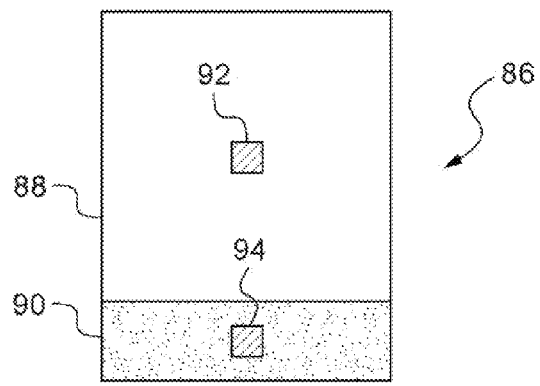

An implementation of the improvement presented in reference to FIGS. 7 and 8 is shown in FIG. 9a. In this figure, a differential pixel 86 comprises a first lighted photosensitive portion 88 and a second darkened photosensitive portion 90. As previously indicated, it is not necessary that the dimensions of the first and second photosensitive portions 88 and 90 are exactly the same, it suffices that the dimensions of collection zones 92 and 94 are the same. It is therefore possible to envisage a large flexibility in the geometry of the differential pixels.

On the other hand, one should to take into consideration the distance that a photoelectron can travel in a substrate before recombining. This distance is called the recombination distance. It is determined first of all by the doping level of the substrate and the by the substrate defects. The more the doping level is high, the less the recombination distance is high. This recombination distance therefore imposes a maximum distance between a collection zone and the edges of the photosensitive portion in which it is located, so that all the photoelectrons can be collected before recombining.

The limited size of the collection zones 92 and 94 therefore imposes a limited size of the photosensitive portions of the differential pixel 86. With a conventional substrate having a resistivity of 100 Ohms per centimeter, the recombination distance is generally between 30 and 50 μm. However, it was previously seen that it is advantageous to plan to have pixels of which the photosensitive surface has dimensions adapted to the size of a drop of a protein probe of several nanoliters allowing detection by chemiluminescence or by fluorescence, that is to say dimensions on the order of 150 μm. With a collection zone 92 the size of which is between 5 and 15 μm, the photosensitive portion 88 cannot reach these dimensions.

Figure 9B:
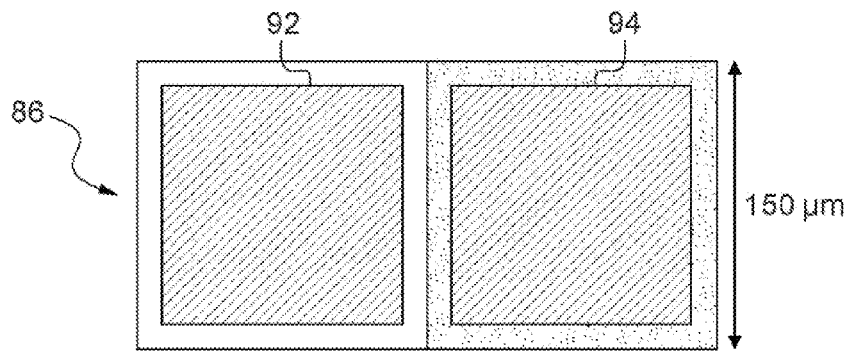

To obtain a differential pixel 86 of larger dimensions, a solution shown in FIG. 9b consists of increasing the size of the collection zones 92 and 94. It is thus possible to obtain pixel dimensions on the order of 150 μm. However, as previously indicated, the increase of the size of the collection zones 92 and 94 increases the effects of the dark current and its associated noise.

To obtain a pixel with larger dimensions, it is also possible to provide several island-shaped n-wells forming collection zones in pixel-type biological analysis device, each spaced one from the other at a distance less than the recombination distance.

In FIG. 9c, a differential pixel 86 comprises two photosensitive portions 88 and 90 each comprising four collection zones 92 and 94 respectively. As shown in this figure, the geometries of these two photosensitive portions 88 and 90 are not necessarily the same. Additionally, the collection zones 92 are not necessarily arranged in the same manner in the lighted photosensitive portion 88 as the collection zones 94 in the darkened photosensitive portion 90. However, the four collection zones 92, on one hand, and the four collection zones 94, on the other hand, have the same dimensions and are for example of 5 or 10 μm. Moreover, the four collection zones 92 are spaced 75 μm one from the other. In this manner, it is possible to obtain a differential pixel 86 the lighted photosensitive portion 88 of which is a square of 150 μm per side and the darkened photosensitive portion 90 of which is a rectangle of 150 μm by 20 μm.

In FIG. 9d, the differential pixel 86 comprises two photosensitive portions 88 and 90 each comprising nine collection zones 92 and 94 respectively. The dimensions of the collection zones 92 and 94 are for example of 5 μm. Moreover, the nine collection zones 92 are spaced 50 μm one from the other for example. In this manner, it is possible to obtain a differential pixel 86 the lighted photosensitive portion 88 of which is a square of 150 μm per side and the darkened photosensitive portion 90 of which is a rectangle of 150 μm by 20 μm.

This can be generalized to pixels (not shown) comprising more collection zones (16 or more).

It can be noted that, because the geometries of the photosensitive portions 88 and 90 are not necessarily the same, the presence of a plurality of collection zones in FIGS. 9c and 9d allows a geometry in which the darkened photosensitive portion 90 surrounds the lighted photosensitive portion 88 to be envisaged.

Provision of an Insulation Joint Between Two Adjacent Pixels

It has been described how the pixels of a biosensor according to the disclosure can be sized in order to correspond with the size of a drop of a protein probe. These advantageous dimensions permit a simpler processing of the obtained signals. However, in order that two neighboring drops of protein probe do not interfere by chemiluminescence or by fluorescence, one can impose a certain minimum distance between two neighboring drops, in general several hundreds of micrometers.

Figure 10:
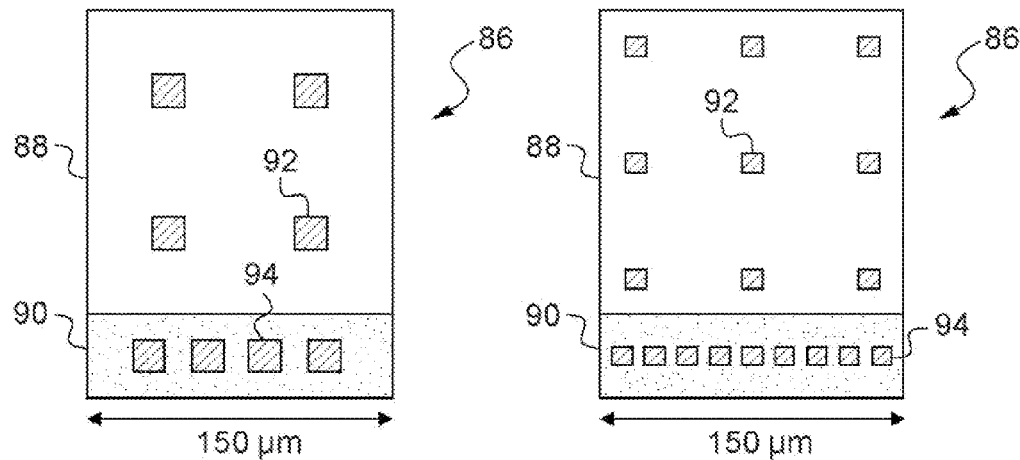
FIG. 10 shows a structure of adjacent pixels usable in a biosensor according to the disclosure.
Figure 10:
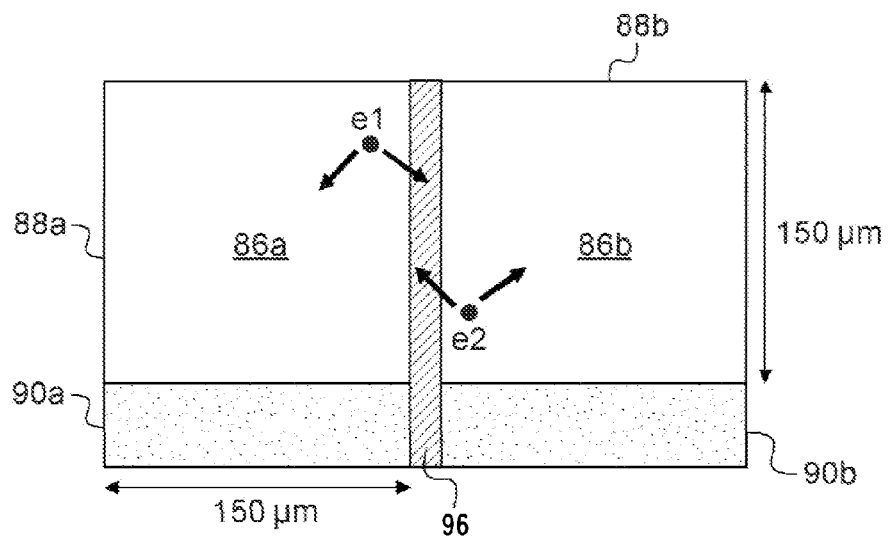

Another improvement of a biosensor according to the disclosure is shown in FIG. 10. This improvement allows for a considerable reduction of the distance between two neighboring drops. This figure shows two neighboring pixels 86a and 86b, sized to each receive a specific protein probe drop. The first pixel 86a comprises a lighted photosensitive portion 88a, here in a square shape, for example of 150 pm per side. It comprises also a darkened photosensitive portion 90a of a rectangular form, 150 μm large and 20 μm wide. The second pixel 86b comprises a lighted photosensitive portion 88b of a square shape of 150 μm per side. It comprises also a darkened photosensitive portion 90b of a rectangular form, 150 μm large and 20 μm wide.

The first pixel 86a is separated from the second pixel 86b by an insulation joint 96 configured to electrically insulate the lighted photosensitive portion 88a of this pixel from the lighted photosensitive portion 88b of the second pixel 86b and to mechanically insulate the two lighted photosensitive portions, such that a source of chemiluminescence or of fluorescence situated in one of the two lighted photosensitive portions is not detected by the other lighted photosensitive portion.

Thus, a photoelectron el emitted in the lighted photosensitive portion 88a, on its border and able to go towards the lighted photosensitive portion 88b, will be absorbed by the insulation joint 96 if it does go towards the lighted photosensitive portion 88b. Reciprocally, a photoelectron e2 emitted in the lighted photosensitive portion 88b, on its border and able to go towards the lighted photosensitive portion 88a, will be absorbed by the insulation joint 96 if it does go towards the lighted photosensitive portion 88a.

Similarly, an excited molecule on the first pixel 86a diffusing a luminous intensity towards the second pixel 86b will have this luminous intensity absorbed by the insulation joint, and vise versa.

To assure a good reciprocal protection between two neighboring pixels, the insulation joint can have a thickness as small as several micrometers or less, which is much less than the size of a pixel or of a drop of protein probe. Therefore, the presence of such an insulation joint 96 allows the pixels of biosensor according to the disclosure to be brought much closer, and thus the number of drops of the specific protein probes that can be deposited on a pre-determined surface of the biosensor can be considerably increased.

The molecules or photoelectrons targeted by the insulation joint 96 are lost for the detection. However, considering the speed of diffusion of molecules emitted by chemiluminescence (or by fluorescence) and the thickness of the insulation joint 96, it can be estimated that a loss of photoelectrons or photons generated on a pixel but not detected by the pixel to be a maximum of 2%, in the least-favorable configuration.

In addition, an insulation joint can also be placed between the photosensitive portions (88a, 90a, and 88b, 90b) of each pixel 86a, 86b and their electronic read circuitry, respectively. In fact, the electronic means are not of the same nature as the photosensitive portions and can be sources of parasitic electrons that contribute to the dark current effects of the photosensitive portions. In addition, the electronic means have a potential higher than that of the photosensitive portions thus attracting the photoelectrons diffusing throughout the photosensitive portions. These phenomena are capable of deteriorating the detection of protein by chemiluminescence or by fluorescence. Therefore, the presence of the insulation joint prevents this migration of undesirable electrons. This insulation joint comprises for example a P+/P− well connected to ground and a N+/N− well connected to a positive voltage.

Fabrication of the Biosensor Sensor

Figure 11A:
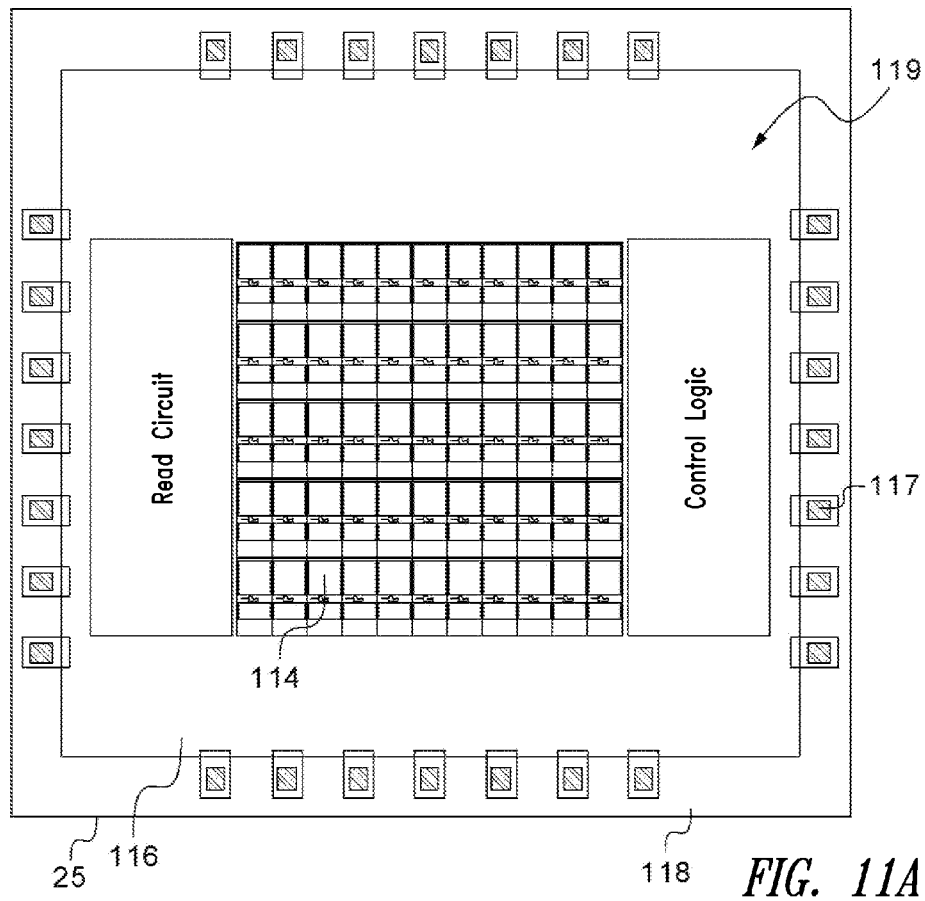
FIGS. 11A, 11B show schematically, by below and cross-sectional views respectively, an embodiment of a biosensor according to the disclosure.

The surface of a biosensor according to the disclosure is shown in FIG. 11a in a view from above. The biosensor is arranged on a semiconductor wafer and comprises a central photosensitive zone 114 configured to be brought into contact with a biological substance, the zone 114 here forming a matrix of pixels of the previously-described type, and a peripheral zone 116 which surrounds the central photosensitive zone 114, the zone 116 comprising various electric circuits (for example digital reading circuits, control logic circuits, etc.) and electric connections between these elements (wiring). Finally, the biosensor comprises contact pads 117 configured for example to permit the wiring of the biosensor ("bonding pads") on an interconnection support. During its fabrication or its utilization, the biosensor is placed in a humid environment, notably in biological solutions or chemical reactants, such as acid/base solutions or oxidizing/reducing. Zone 116 is thus susceptible of being in contact with a humid environment, which can damage the electric areas that it contains.

An improvement aimed at here is to protect zone 116 from humid environments intended to be in contact with the central photosensitive zone 114, and also to promote the deposition of the capture mixture as described above. This improvement comprises supplying the following measures or steps, during the fabrication of the biosensor:

separating the contact pads 117 from the central photosensitive zone 114, for example at a distance of 850 micrometers, by placing them in a peripheral zone 118 that surrounds the peripheral zone 116. This separation prevents their contact with liquids during the chemical treatments of the sensor or during the biological testing;

covering the peripheral zone 116 with a hydrophilic coating with a high roughness. This hydrophilic coating is for example silicon oxide ($SiO_2$) and forms a sort of "ring", for example with a width of approximately 700 µm, around the central photosensitive zone 114;

covering the central photosensitive zone 114 with a hydrophobic coating with a low roughness, for example silicon nitride ($Si3N4$).

Preferably, the rest of the surface of the biosensor is equally covered with the hydrophobic coating with a low roughness, so that the peripheral zone 118 and zone 114 can be simultaneously treated.

This coating allows for a distinct demarcation between the peripheral zone 116 to be protected and the central photosensitive zone 114.

Figure 11B:
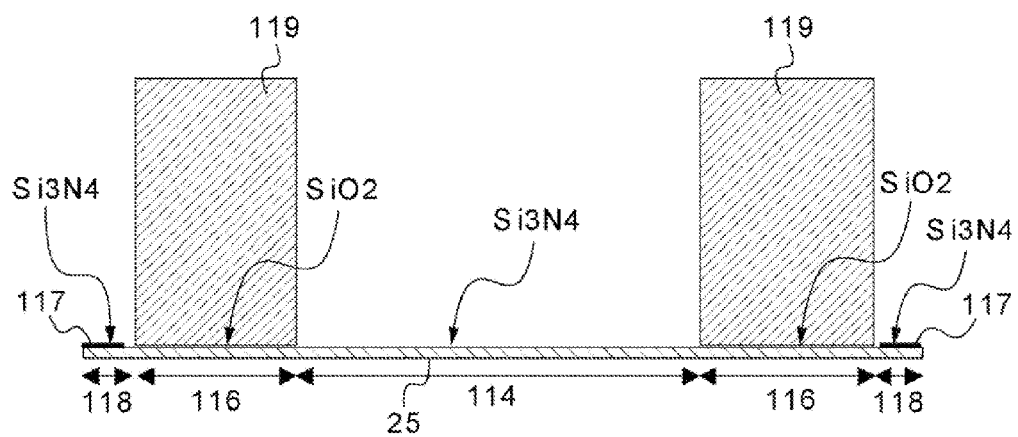

Once these steps are performed, the peripheral zone 116 can be covered with a thick resin layer 119 bio-compatible and non-conducting, forming a sort of barrier which completely encircles the central zone, as shown in FIG. 11B in a cross-sectional view. This resin barrier is insulated from the humid environment of zone 118 with the contact pads 117 all while equally protecting the wiring zone 116, which it covers completely. Its height can be several millimeters and is thus much greater than the thickness of the biosensor, which is for example 30 to 100 µm.

Thanks to the hydrophilic variation between the zones 116 and 114, 118, the protective resin 119 has the tendency, before hardening due to polymerization, to automatically spread all around the central photosensitive zone 114, without encroaching upon nor adhering to the central photosensitive zone and without covering the contact pads 117. In other words, the treatment of the hydrophobic surface has a "repulsive" effect vis-à-vis the resin and limits its spreading, until the resin is polymerized.

The hydrophobic coating on the central photosensitive zone 114 also assures that the solutions deposited on zone 114 during the steps of the biological preparation are not spread beyond the pixel matrix by chemically attacking the elements belonging to zone 116 and are found within the interior border of zone 116. Such elements situated within the border of zone 116, for example aluminum conductors, could be imperfectly covered by the resin 119 and thus are imperfectly protected.

In particular, the formation process of the hydrogel such as described above can comprise the step S104 of deposition of a potassium hydroxide solution (KOH) that is susceptible of chemically attacking the fragile elements on the border of zone 116. The solution is deposited on the pixel matrix according to a determined dosage. The hydrophobic coating prevents that the dose of the potassium hydroxide solution spreads beyond the central photosensitive zone 114, under the effect of superficial tensions.

By way of example, a roughness on the order of 50 nm was measured on a silicon nitride ($Si3N4$) coating by using conventional roughness depth measurement techniques. The silicon nitride solution was deposited by using a conventional fabrication process implemented in production units of the applicant, and allowed the desired result to be obtained by limiting the spreading of the potassium hydroxide solution. The skilled person can nevertheless determine other coatings and treatment processes that allow the central photosensitive zone 114 to become hydrophobic.

Thus, the combination of these features permits optimal deposition and adherence of the protective resin 119, both by the chemical characteristics of the treated surfaces and by the disposition of components of the biosensor and their spacing.

It will clearly appear to the skilled person that a biological analysis device and a biosensor according to the disclosure, to which are eventually added the previously-described improvements, allow the utilization of CMOS imager technology for the analysis by chemiluminescence or by fluorescence of biological substances comprising the fragile target protein. It will also appear to the skilled person that the various embodiments as well as the various improvements previously described can be combined in order to obtain other embodiments. In addition, the skilled person may provide various modifications to the embodiments described above, in the light of the teaching that has been disclosed. In the claims, the terms utilized should not be interpreted as limiting the claims to the embodiments disclosed in the present description, but should be interpreted to include all equivalents that the claims aim to cover in that their formulation and anticipation is within the reach of skilled persons by applying their general knowledge to the implementation of the teaching that has just been disclosed.

The various embodiments described above can be combined to provide further embodiments. All of the U.S. patents, U.S. patent application publications, U.S. patent application, foreign patents, foreign patent application and non-patent publications referred to in this specification are incorporated herein by reference, in their entirety. Aspects of the embodiments can be modified to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A pixel-type biological analysis device comprising:
a photosensitive layer;
a capture mixture configured to capture targeted proteins, the capture mixture being positioned on an external surface of the photosensitive layer and including a hydrogel and a protein probe grafted to the hydrogel;
a photoelectron collector in the photosensitive layer and configured to collect photoelectrons and provide an electrical quantity, wherein the photoelectron collector comprises:
a first portion configured to detect an incident luminous intensity coming from the capture mixture and supply a first electrical quantity; and
a second portion configured to supply a second electrical quantity and protected against all sources of luminous intensity, including the incident luminous intensity coming from the capture mixture; and
read circuitry configured to read the electrical quantity and supply a read signal characteristic of a luminous intensity detected by the photosensitive layer, wherein the read circuitry includes an amplifier having a first input coupled to the first portion and a second input coupled to the second portion, the amplifier being configured to supply a read signal based on the first and second electrical quantities, the read signal being characteristic of the incident luminous intensity detected by the first portion.

2. A biological analysis device according to claim 1, in which an external surface of the photosensitive layer is of a sufficient size to receive an entire drop of the protein probe.

3. A biological analysis device according to claim 2, in which the external surface of the photosensitive layer has an area of at least $25500 \times 10^{-12}$ m$^2$.

4. A biological analysis device according to claim 1, in which the photoelectron collector includes plural island-shaped collection zones spaced from each other in the photosensitive layer.

5. A biological analysis device according to claim 4, in which the collection zones are spaced from each other in the photosensitive layer at a distance less than a recombination distance of photoelectrons to be emitted in the photosensitive layer.

6. A process of fabricating a biological analysis device, comprising:
making a photosensitive layer;
making a capture mixture configured to capture targeted proteins, the capture mixture being positioned on an external surface of the photosensitive layer and including a protein probe grafted to a hydrogel;
making a photoelectron collector in the photosensitive layer and configured to collect photoelectrons, wherein making the photoelectron collector comprises:
making a first portion configured to detect an incident luminous intensity coming from the capture mixture and supply a first electrical quantity; and
making a second portion configured to supply a second electrical quantity and protected against all sources of luminous intensity, including the incident luminous intensity coming from the capture mixture; and
making read circuitry configured to read an electrical quantity supplied by the photoelectron collector and supply a read signal characteristic of a luminous intensity detected by the photosensitive layer, wherein the read circuitry includes an amplifier having a first input coupled to the first portion and a second input coupled to the second portion, the amplifier being configured to supply a read signal based on the first and second electrical quantities, the read signal being characteristic of the incident luminous intensity detected by the first portion.

7. A process according to claim 6, comprising:
preparing the external surface of the photosensitive layer, the preparing including silanizing the external surface, wherein making the capture mixture includes:
oxidizing the hydrogel and grafting the oxidized hydrogel on the silanized external surface;
carboxylizing and activating the grafted hydrogel; and
grafting the protein probe in the activated hydrogel.

8. A process according to claim 7, in which preparing the external surface comprises:
cleaning the external surface by successive rinsings with demineralized water, acetone and ethanol in an ultrasonic bath;
alkaline oxidizing the external surface under an ozone plasma, then treating with a solution of potassium hydroxide during several hours at an ambient temperature;
successively submerging the external surface in demineralized water, then in ethanol under ultrasound, and drying under an Argon flow;
silanizing the external surface via a solution of 3-aminopropyltriethoxysilane in ethanol during several hours;
successively submerging the external surface in demineralized water, then in ethanol under ultrasound, and drying under an Argon flow; and
heating the external surface during several hours, then maintaining under an inert atmosphere.

9. A process according to claim 7, in which oxidizing the hydrogel and grafting the oxidized hydrogel include:
obtaining a reaction mixture having molar ratio between sodium periodate and repeated monomers of the hydrogel on the order of 50%, the obtaining including dissolving the hydrogel in demineralized water, then treating with a solution of sodium periodate;

obtaining the oxidized hydrogel by protecting the obtained reaction mixture against light and agitating during several hours at ambient temperature;

grafting the oxidized hydrogel on the silanized external surface and agitating at ambient temperature and protected from light during several hours; and treating the grafted oxidized hydrogel with an aqueous solution of sodium cyanoborohydride during several hours in order to reduce formed Schiff bases, then rinsing in demineralised water and ethanol, and drying under Argon flow.

10. A process according to claim 7, in which carboxilizing and activating the grafted hydrogel comprises:

obtaining a reaction mixture by treating the grafted hydrogel with a solution of bromoacidic acid in sodium periodate during several hours at ambient temperature and under Argon;

draining the reaction mixture, then rinsing in demineralized water and ethanol, and drying under Argon flow; and activating in esters of formed carboxylate residue, then rinsing with water.

11. A process according to claim 7, comprising treating the external surface of the photosensitive layer, prior to making the capture mixture, with a hydrophobic coating having a roughness chosen such that at least one solution deposited on the photosensitive layer during making the capture mixture does not spread out beyond the photosensitive layer.

12. A process according to claim 6, comprising sizing the external surface of the photosensitive layer to correspond to a drop of the capture mixture.

13. A biosensor comprising:

a plurality of pixel-type biological analysis devices arranged in a matrix of pixels, each pixel-type biological analysis device including:

a photosensitive layer;

a capture mixture configured to capture targeted proteins, the capture mixture being positioned on an external surface of the photosensitive layer and including a hydrogel and a protein probe grafted to the hydrogel;

a photoelectron collector in the photosensitive layer and configured to collect photoelectrons and provide an electrical quantity, wherein the photoelectron collector comprises:

a first portion configured to detect an incident luminous intensity coming from the capture mixture and supply a first electrical quantity; and a second portion configured to supply a second electrical quantity and protected against all sources of luminous intensity, including the incident luminous intensity coming from the capture mixture; and read circuitry configured to read the electrical quantity and supply a read signal characteristic of a luminous intensity detected by the photosensitive layer, wherein the read circuitry includes an amplifier having a first input coupled to the first portion and a second input coupled to the second portion, the amplifier being configured to supply a read signal based on the first and second electrical quantities, the read signal being characteristic of the incident luminous intensity detected by the first portion; and a processing circuit configured to process each read signal output by the matrix of pixels.

14. A biosensor according to claim 13, in which:

each pixel of the matrix of pixels comprises an analog to digital converter configured to digitally convert the read signal of the pixel; and the processing circuit comprises a digital data transmission bus connected to the analog to digital converters of pixels of the matrix.

15. A biosensor according to claim 13, comprising a plurality of insulating joints respectively configured to electrically insulate from each other the photosensitive layers of adjacent pixels of each of a plurality of pairs of the pixels of the matrix.

16. A biosensor according to claim 13, comprising:

a central zone in which the matrix of pixels is arranged;

a first hydrophobic coating covering the central zone;

a first peripheral zone surrounding the central zone and including electronic circuits;

a hydrophilic coating covering the first peripheral zone;

a second peripheral zone surrounding the first peripheral zone and including electric contact pads;

a second hydrophobic coating covering the electric contact pads; and a bio-compatible resin barrier covering the first peripheral zone and fixed on the hydrophilic coating.

17. A biosensor according to claim 16, in which the hydrophilic coating is silicon oxide.

18. A biosensor according to claim 16, in which the hydrophobic coating is silicon nitride.

* * * * *